US012224071B2

(12) United States Patent
Kiljanek

(10) Patent No.: US 12,224,071 B2
(45) Date of Patent: Feb. 11, 2025

(54) GENERATION OF SIMULATED PATIENT DATA FOR TRAINING PREDICTED MEDICAL OUTCOME ANALYSIS ENGINE

(71) Applicant: Lukasz R. Kiljanek, Chesapeake Beach, MD (US)

(72) Inventor: Lukasz R. Kiljanek, Chesapeake Beach, MD (US)

( * ) Notice: Subject to any disclaimer, the term of this patent is extended or adjusted under 35 U.S.C. 154(b) by 587 days.

(21) Appl. No.: 16/599,109

(22) Filed: Oct. 10, 2019

(65) Prior Publication Data
US 2020/0118691 A1 Apr. 16, 2020

Related U.S. Application Data

(60) Provisional application No. 62/743,789, filed on Oct. 10, 2018.

(51) Int. Cl.
*G16H 50/50* (2018.01)
*G06N 20/20* (2019.01)
*G16H 50/20* (2018.01)

(52) U.S. Cl.
CPC ............. *G16H 50/50* (2018.01); *G06N 20/20* (2019.01); *G16H 50/20* (2018.01)

(58) Field of Classification Search
CPC ......... G16H 10/00–80/00; G06N 3/00–99/007
See application file for complete search history.

(56) References Cited

U.S. PATENT DOCUMENTS 8,775,332 B1 * 7/2014 Morris ...................... G06N 5/02
706/11
10,171,311 B2 * 1/2019 Harvey ..................... G06F 16/21
10,460,235 B1 * 10/2019 Truong ..................... G06N 5/00
(Continued)

FOREIGN PATENT DOCUMENTS

WO WO-2005067662 A2 * 7/2005 ............. G06Q 10/00
WO WO-2006084196 A2 * 8/2006 ........... G06F 19/324
(Continued)

OTHER PUBLICATIONS

Palmer et al., "The CORE Diabetes Model: Projecting Long-term Clinical Outcomes, Costs and Costeffectiveness of Interventions in Diabetes Mellitus (Types 1 and 2) to Support Clinical and Reimbursement Decisionmaking," Current Medical Research and Opinion® vol. 20, Suppl 1, 2004, S5-S26 (Year: 2004).*
(Continued)

*Primary Examiner* — Jonathon A. Szumny
(74) *Attorney, Agent, or Firm* — Polsinelli LLP

(57) ABSTRACT

A system receives feature parameters, each identifying possible values for one of a set of features. The system receives outcomes corresponding to the feature parameters. The system generates a simulated patient population dataset with multiple simulated patient datasets, each simulated patient dataset associated with the outcomes and including feature values falling within the possible values identified by the feature parameters. The system may train a machine learning engine based on the simulated patient population dataset and optionally additional simulated patient population datasets. The machine learning engine generates predicted outcomes based on the training in response to queries identifying feature values.

80 Claims, 18 Drawing Sheets

(56) References Cited

U.S. PATENT DOCUMENTS

| | | | | |
|---|---|---|---|---|
| 2004/0225200 | A1* | 11/2004 | Edmundson | G16Z 99/00 128/923 |
| 2006/0154276 | A1* | 7/2006 | Lois | A61P 1/04 435/6.17 |
| 2008/0131439 | A1* | 6/2008 | Lois | A61K 31/4985 514/263.1 |
| 2010/0191071 | A1* | 7/2010 | Anderson | G16Z 99/00 703/11 |
| 2010/0324874 | A9 | 12/2010 | Bangs et al. | |
| 2013/0288215 | A1* | 10/2013 | Butler | G06Q 10/10 703/11 |
| 2014/0095204 | A1 | 4/2014 | Fung et al. | |
| 2015/0370992 | A1* | 12/2015 | Yao | G16H 50/70 703/2 |
| 2016/0073969 | A1* | 3/2016 | Ithapu | A61B 6/4417 382/128 |
| 2016/0196384 | A1* | 7/2016 | Mansi | G16H 30/20 600/408 |
| 2016/0253473 | A1 | 9/2016 | Anderson et al. | |
| 2016/0379139 | A1* | 12/2016 | Eldar | G06F 16/35 706/12 |
| 2017/0308671 | A1* | 10/2017 | Bahrami | G16H 10/60 |
| 2018/0004905 | A1 | 1/2018 | Szeto | |
| 2018/0071452 | A1* | 3/2018 | Sharma | A61M 5/007 |
| 2018/0107729 | A1* | 4/2018 | Vyas | G06N 20/00 |
| 2018/0122506 | A1 | 5/2018 | Grantcharov et al. | |
| 2018/0182101 | A1* | 6/2018 | Petersen | G06T 7/0014 |
| 2018/0247020 | A1* | 8/2018 | Itu | G06N 20/00 |
| 2018/0247714 | A1* | 8/2018 | Lee | A61B 5/055 |
| 2018/0315182 | A1* | 11/2018 | Rapaka | G06N 5/04 |
| 2018/0336319 | A1* | 11/2018 | Itu | G06K 9/6267 |
| 2019/0026654 | A1* | 1/2019 | Allen | G06N 20/00 |
| 2019/0059998 | A1* | 2/2019 | Mei | G06N 3/006 |
| 2019/0065666 | A1* | 2/2019 | Wong | G16B 5/00 |
| 2019/0127798 | A1* | 5/2019 | Hagstrom | G16B 40/20 |
| 2019/0139641 | A1* | 5/2019 | Itu | G06N 3/0472 |
| 2019/0171911 | A1* | 6/2019 | Greenberg | G06N 3/084 |
| 2019/0392926 | A1* | 12/2019 | Koh | G06F 40/40 |
| 2020/0027554 | A1* | 1/2020 | Boroczky | G16H 30/40 |
| 2020/0242466 | A1* | 7/2020 | Mohassel | G06N 3/084 |
| 2021/0085397 | A1* | 3/2021 | Passerini | G16H 50/30 |

FOREIGN PATENT DOCUMENTS

| | | | | |
|---|---|---|---|---|
| WO | WO-2011091059 | A1 * | 7/2011 | G16H 50/20 |
| WO | WO-2015066421 | A1 * | 5/2015 | G16H 10/60 |
| WO | WO-2016075331 | A2 * | 5/2016 | A61B 5/026 |
| WO | WO-2016180953 | A1 * | 11/2016 | A61B 5/02 |
| WO | WO-2019055336 | A1 * | 3/2019 | A61B 5/0022 |
| WO | WO 2020/077163 | | 4/2020 | |

OTHER PUBLICATIONS

Walonoski et al., "Synthea: An approach, method, and software mechanism for generating synthetic patients and the synthetic electronic health care record," Journal of the American Medical Informatics Association, 25(3), 2018, 230-238 doi: 10.1093/jamia/ocx079; Advance Access Pub. Date: Aug. 30, 2017. (Year: 2017).*

Choi et al., "Generating Multi-label Discrete Patient Records using Generative Adversarial Networks," Proceedings of Machine Learning for Healthcare 2017 JMLR W&C Track vol. 68. (Year: 2017).*

PCT Application No. PCT/US2019/055747 International Preliminary Report on Patentability dated Apr. 8, 2021.

PCT Application No. PCT/US2019/055747 International Search Report and Written Opinion dated Dec. 23, 2019.

* cited by examiner

FIG. 7B predicted outcomes 730 generated based on query dataset 710

Likely diagnoses with probabilities 735
- COPD 740A (likelihood probability 742A: 70%)
- Lung cancer 740B (likelihood probability 742B: 65%)
- Asthma 740C (likelihood probability 742C: 10%)
- Flu 740D (likelihood probability 742D: 5%)

Recommended tests 745
- Pulmonary function test 750A (strength of rec 752A: 42%)
- Complete blood count 750B (strength of rec 752B: 10%)
- MRI 750C (strength of rec 752C: 6%)

Features factoring most into 70% COPD diagnosis 755
- Heavy cough 760A (effect on likelihood of diagnosis 762A: +24%)
- Normal chest X-ray 760B (effect on likelihood of diagnosis 762B: +21%)
- History of smoking 760C (effect on likelihood of diagnosis 762C: +20%)

Features factoring most into 65% lung cancer diagnosis 765
- History of smoking 770A (effect on likelihood of diagnosis 772A: +30%)
- Heavy cough 770B (effect on likelihood of diagnosis 772B: +24%)
- Normal chest X-ray 770C (effect on likelihood of diagnosis 772C: -11%)

Features factoring most into 10% asthma diagnosis 775
- Lack of wheezing 780A (effect on likelihood of diagnosis 782A: -20%)
- Heavy cough with mucus 780B (effect on likelihood of diagnosis 782B: -13%)
- Normal chest X-ray 780C (effect on likelihood of diagnosis 782C: -11%)

Follow-on questions 785
- Question 790A: is there family history of lung cancer? (click to answer)
- Question 790B: is the patient male or female? (click to answer)

Recommended treatments 792
- Drug 795A (strength of recommendation 798A: 35%)
- Surgery 795B (strength of recommendation 798B: 12%)
- Vitamins 795C (strength of recommendation 798C: 4%)

FIG. 8

> Example 800 of expert UI 115 analyzing information source 810 for assisted NLP mode 170

- Source 815: National Center for Biotechnology Information (hyperlink)
- Type of source 820: abstract, journal, publication.
- Outcome 825: Lung cancer diagnosis (in knowledge database, Outcome ID is "LungCa")

NLP algorithm found the following features in the document:

"Hemoptysis" – symptom, odds ratio for having outcome 825 6:39
Categorical feature values, possible category values for the feature: "yes", "no".
New feature, not available in knowledge database.
(click here to choose the way it will be handled)
(click here to edit categories, current : "yes"/"no")
(click here to edit "odds ratio": current  6:39 )
(☑ check here to keep this Feature)

"Dyspnea" – symptom, odds ratio for having outcome 825 2:73
Categorical feature values, possible category values for the feature: "yes", "no".
New feature, not available in knowledge database.
(click here to choose the way it will be handled)
(click here to edit categories, current : "yes"/"no")
(click here to edit "odds ratio": current  2:73 )
(☑ check here to keep this Feature)

"Cough" – symptom, odds ratio for having outcome 825 2:64
Categorical feature values, possible category values for the feature: "yes", "no".
This feature is already in knowledge database, under the Feature ID "Cough"
(click here to choose the way it will be handled)
(click here to edit categories, current : "yes"/"no")
(click here to edit "odds ratio": current  2:64 )
(☑ check here to keep this Feature)

"Chest pain" – symptom, odds ratio for having outcome 825 2:20
Categorical feature values, possible category values for the feature: "yes", "no".
This feature is likely already in knowledge database, under the Feature ID "Chest pains"
(click here to choose the way it will be handled)
(click here to edit categories, current : "yes"/"no")
(click here to edit "odds ratio": current  2:20 )
(☑ check here to keep this Feature)

(click here to add to all "checked as kept" Features to knowledge database as categorical Features maintaining odds ratios found in information source)
(click here to create new Outcome ID for "LungCa")

FIG. 10

Example 1000 of expert user interface 115 for generating patient population source seed 120

Feature parameters 1002 for simulated patients in simulated patient population dataset 1005:

Genders 1010:
☑ Male
☑ Female
☐ Other
☐ NA

Age 1015: 18 — 47 — 91 — 120

Body temp (°F) 1020: 95 — 96 — 100 — 106

BMI 1025: 12 — 27 — 45 — 60

Pulse rate (bpm) 1030: 0 — 60 — 95 — 220

Systolic blood pressure 1035: 0 — 100 — 139 — 270

Distolic blood pressure 1040: 0 — 50 — 84 — 180

Respiratory rate 1045: 0 — 12 — 18 — 60

Arterial O₂ Sat (SaO2%) 1050: 0 — 94 — 100

Supplied air O₂ % (FiO2%) 1055:
Room air: 21%, Nasal canula: 1L/min 24%, 2L/min 28%, 3L/min 32%, 4L/min 36%, 5L/min 40%, 6L/min 44%
21 — 27 — 100

Outcomes 1060 corresponding to the feature parameters 1002:

Acute diagnoses 1065:

[Pneumonia (Pulmunary)] [Pulmunary embolus (Pulmunary)] [CAN'T MISS!]

Recommended tests 1070:

[Chest CT scan with IV dye]

Chronic diagnoses 1075:

[Chronic Nontuberculous mycobacteria lung infection (Pulmunary)]
Chronic COPD
Chronic Asthma
Churg-Strauss syndrome
Chronic left ventricle heart failure (LVHF)
Hypertrophic cardiomyopathy
Dilated cardiomyopathy
Chronic tricuspid regurgitation (TR)

Count 1080: [5,000]

FIG. 12A $\qquad$ ⸺ 1200

| Age | SmokerHx | Cough | Hemoptysis | LungCa | Health | BeningChronicCough | ChestXRayPALat | PortableCxray |
|---|---|---|---|---|---|---|---|---|
| 54.46 | 285.02 | 2 | 3 | 1 | 0 | 0 | 1 | 0 |
| 124.66 | 198.72 | 2 | 3 | 1 | 0 | 0 | 1 | 0 |
| 112.07 | 240.3 | 2 | 2 | 1 | 0 | 0 | 1 | 0 |
| 121.81 | 180.1 | 3 | 3 | 1 | 0 | 0 | 1 | 0 |
| 92.99 | 280.2 | 3 | 3 | 1 | 0 | 0 | 1 | 0 |
| 99.85 | 260.17 | 2 | 3 | 1 | 0 | 0 | 1 | 0 |
| 113.18 | 252.81 | 2 | 3 | 1 | 0 | 0 | 1 | 0 |
| 80.82 | 290.71 | 2 | 2 | 1 | 0 | 0 | 1 | 0 |
| 127.54 | 105.94 | 2 | 3 | 1 | 0 | 0 | 1 | 0 |
| 102.11 | 264.33 | 3 | 3 | 1 | 0 | 0 | 1 | 0 |
| 69 | 0 | 2 | 2 | 0 | 1 | 0 | 0 | 0 |
| 55 | 0 | 2 | 2 | 0 | 1 | 0 | 0 | 0 |
| 5 | 0 | 2 | 2 | 0 | 1 | 0 | 0 | 0 |
| 65 | 0 | 2 | 2 | 0 | 1 | 0 | 0 | 0 |
| 66 | 0 | 2 | 2 | 0 | 1 | 0 | 0 | 0 |
| 81 | 0 | 2 | 2 | 0 | 1 | 0 | 0 | 0 |
| 69 | 0 | 2 | 2 | 0 | 1 | 0 | 0 | 0 |
| 8 | 0 | 2 | 2 | 0 | 1 | 0 | 0 | 0 |
| 25 | 0 | 2 | 2 | 0 | 1 | 0 | 0 | 0 |
| 4 | 0 | 2 | 2 | 0 | 1 | 0 | 0 | 0 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |
| 35 | 0 | 3 | 2 | 0 | 0 | 1 | 1 | 1 |

| Age | SmokerHx | Cough | Hemoptysis | LungCa | Health | BeningChronicCough | ChestXRayPALat | PortableCxray |
|---|---|---|---|---|---|---|---|---|
| 106.72 | 103.22 | 3 | 3 | 1 | 0 | 0 | 1 | 0 |
| 118.18 | 177.22 | 2 | 2 | 1 | 0 | 0 | 1 | 0 |
| 98.28 | 144.46 | 3 | 2 | 1 | 0 | 0 | 1 | 0 |
| 107.67 | 166.38 | 3 | 3 | 1 | 0 | 0 | 1 | 0 |
| 93.4 | 152.32 | 3 | 2 | 1 | 0 | 0 | 1 | 0 |
| 114.16 | 205.25 | 2 | 3 | 1 | 0 | 0 | 1 | 0 |
| 110.25 | 255.6 | 2 | 3 | 1 | 0 | 0 | 1 | 0 |
| 112.19 | 183.24 | 2 | 3 | 1 | 0 | 0 | 1 | 0 |
| 56.64 | 299.03 | 2 | 3 | 1 | 0 | 0 | 1 | 0 |
| 117.68 | 275.18 | 3 | 3 | 1 | 0 | 0 | 1 | 0 |
| 42 | NA | NA | NA | 0 | 1 | 0 | 0 | 0 |
| 79 | NA | NA | NA | 0 | 1 | 0 | 0 | 0 |
| 61 | NA | NA | NA | 0 | 1 | 0 | 0 | 0 |
| 74 | NA | NA | NA | 0 | 1 | 0 | 0 | 0 |
| 25 | NA | NA | NA | 0 | 1 | 0 | 0 | 0 |
| 89 | NA | NA | NA | 0 | 1 | 0 | 0 | 0 |
| 58 | NA | NA | NA | 0 | 1 | 0 | 0 | 0 |
| 87 | NA | NA | NA | 0 | 1 | 0 | 0 | 0 |
| 99 | NA | NA | NA | 0 | 1 | 0 | 0 | 0 |
| 18 | NA | NA | NA | 0 | 1 | 0 | 0 | 0 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |
| NA | NA | 3 | 2 | 0 | 0 | 1 | 1 | 1 |

FIG. 14A

Outcome 1405: Lung cancer diagnosis

Relevant Features 1410:
| Name | Distribution |
|---|---|
| Age | gaussian \| 130, 30, 0, 130 |
| SmokerHx | gaussian \| 300, 100, 0, 300 |
| Hemoptysis | category \| 1:0, 2:20, 3:80 |
| Cough | category \| 1:0, 2:40, 3:60 |

Highlighted feature 1415: Cough

Possible feature values 1420 for cough feature:
- 1 = data unavailable
- 2 = no cough present
- 3 = yes, cough present Count 1425: 10

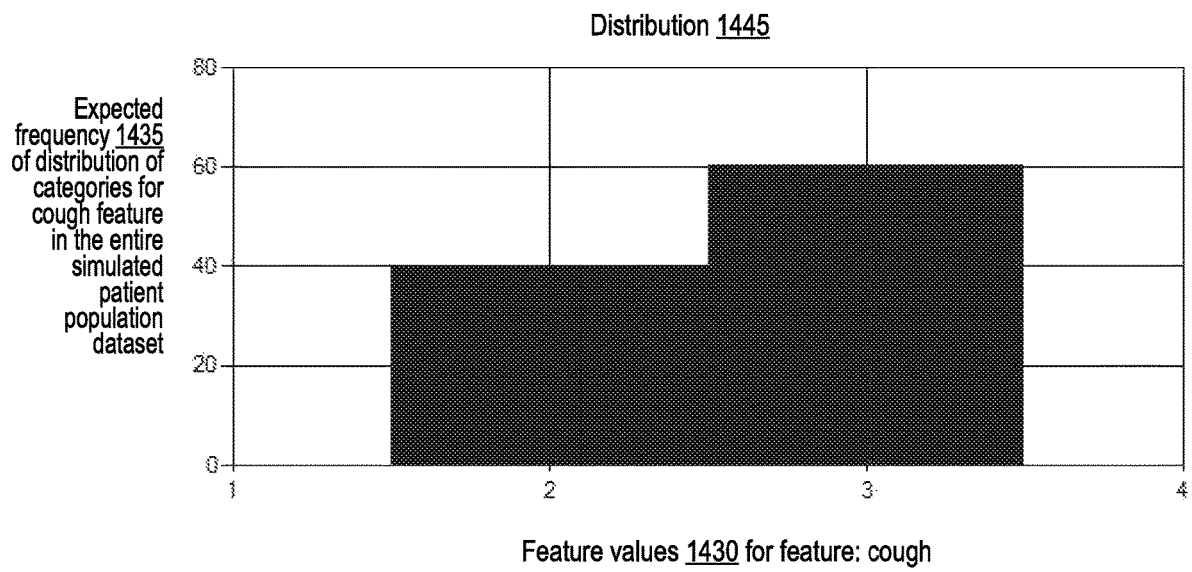

Expected frequency 1435 of distribution of categories for cough feature in the entire simulated patient population dataset Distribution 1445

Feature values 1430 for feature: cough

1450

Outcome 1405: Lung cancer diagnosis

Relevant Features 1410:
| Name | Distribution |
|---|---|
| Age | gaussian \| 130, 30, 0, 130 |
| SmokerHx | gaussian \| 300, 100, 0, 300 |
| Hemoptysis | category \| 1:0, 2:20, 3:80 |
| Cough | category \| 1:0, 2:40, 3:60 |

Highlighted feature 1460: Age

Count 1465: 100

Distribution 1485

Expected frequency 1475 of distribution of values for the age feature in the entire simulated patient population dataset Feature values 1470 for feature: age

GENERATION OF SIMULATED PATIENT DATA FOR TRAINING PREDICTED MEDICAL OUTCOME ANALYSIS ENGINE

CROSS-REFERENCE TO RELATED APPLICATIONS

The present application claims the priority benefit of U.S. provisional application No. 62/743,789 filed Oct. 10, 2018 and entitled "Knowledge Database System and Methods," the disclosure of which is hereby incorporated by reference.

BACKGROUND

1. Field

The present teachings are generally related to automated medical outcome prediction. More specifically, the present teachings relate to automated generation of a simulated patient population dataset and use of the simulated patient population dataset to train a machine learning engine for an automated medical outcome prediction system.

2. Description of the Related Art

Medical professionals, such as doctors, need to issue numerous medical diagnoses and order various tests and treatments during the course of their work. A medical professional typically must undergo many years of postgraduate education and on-the-job training to be qualified to accurately diagnose or treat a patient's condition based on symptoms, test results, and other characteristics of the patient. However, qualified medical professionals with expertise relevant to a patient's issue are often in short supply, especially in developing countries, rural areas, or on military deployments. As a result, medical professionals in some regions or circumstances are sometimes required to issue diagnoses and perform procedures that are outside of their areas of expertise, which can lead to missed diagnoses, delayed diagnoses, incorrect diagnoses, missed treatments, delayed treatments, or incorrect treatments. The stakes of misdiagnosing or mistreating patients are very high—each of these situations can worsen a patient's health and in some cases can lead to the patient's death.

Traditional medical data, such as personal, health-related, demographic, and biometric data collected from patients, is considered extremely sensitive. Privacy of medical data, and security of systems that handle medical data, are both highly regulated by governments worldwide. As a result, medical data from patients or medical studies is traditionally kept securely in computer systems belonging to hospitals, health insurance companies, or pharmaceutical companies. Researchers and other medical professionals generally cannot access such medical data, and especially not in any useful quantity or form. In some cases, medical data may be "anonymized" through removal of patient names and other explicitly identifying information, a tedious process that often requires considerable manual labor, as medical data is often not uniformly formatted and can come from disparate sources. Even when medical data is anonymized through removal of explicitly identifying information, however, privacy concerns may still remain, as a patient's identity may sometimes still be deduced based on physical characteristics, symptoms, and other features described in the patient's medical data. As a result, researchers and other medical professionals have largely been prevented from developing systems that analyze or draw insights based on patient medical data.

SUMMARY

Techniques and systems are described herein for generating a simulated patient population dataset with one or more simulated patient datasets based on feature parameters and outcomes. Each simulated patient dataset is associated with the outcomes and includes feature values for various features, the feature values based on the feature parameters. A machine learning engine is trained using at least the simulated patient population dataset. The predicted outcomes based on the training in response to queries identifying feature values.

In one example, a method for generating and processing simulated patient information is provided that includes receiving one or more feature parameters corresponding to one or more features. Each feature parameter of the one or more feature parameters identifies one or more possible values for one feature of the one or more features. The method also includes receiving one or more outcomes corresponding to the one or more feature parameters. The method also includes generating a simulated patient population dataset that includes one or more simulated patient datasets. Each simulated patient dataset of the one or more simulated patient datasets includes one or more feature values corresponding to the one or more features. The one or more feature values are generated such that each feature value of the one or more feature values is selected from the one or more possible values for each feature of the one or more features. Each simulated patient dataset of the one or more simulated patient datasets is associated with the one or more outcomes. The method also includes training a machine learning engine based on the simulated patient population dataset. The machine learning engine generates one or more predicted outcomes based on the training, wherein the machine learning engine generates one or more predicted outcomes based on the training.

In another example, a system that generates and processes simulated patient information is provided. The system includes one or more communication transceivers that receive one or more feature parameters corresponding to one or more features. Each feature parameter of the one or more feature parameters identifies one or more possible values for one feature of the one or more features. The one or more communication transceivers also receive one or more outcomes corresponding to the one or more feature parameters. The system also includes one or more memory units storing instructions and one or more processors that execute the instructions. Execution of the instructions by the one or more processors causes the one or more processors to perform operations. The operations include generating a simulated patient population dataset that includes one or more simulated patient datasets. Each simulated patient dataset of the one or more simulated patient datasets includes one or more feature values corresponding to the one or more features. The one or more feature values are generated such that each feature value of the one or more feature values is selected from the one or more possible values for each feature of the one or more features. Each simulated patient dataset of the one or more simulated patient datasets is associated with the one or more outcomes. The operations also include training a machine learning engine based on the simulated patient population dataset. The machine learning engine generates one or more predicted outcomes based on the training, wherein the machine learning engine generates one or more predicted outcomes based on the training.

In another example, a non-transitory computer readable storage medium having embodied thereon a program is provided. The program is executable by a processor to perform a method of generating and processing simulated patient information. The method includes receiving one or more feature parameters corresponding to one or more features. Each feature parameter of the one or more feature parameters identifies one or more possible values for one feature of the one or more features. The method also includes receiving one or more outcomes corresponding to the one or more feature parameters. The method also includes generating a simulated patient population dataset that includes one or more simulated patient datasets. Each simulated patient dataset of the one or more simulated patient datasets includes one or more feature values corresponding to the one or more features. The one or more feature values are generated such that each feature value of the one or more feature values is selected from the one or more possible values for each feature of the one or more features. Each simulated patient dataset of the one or more simulated patient datasets is associated with the one or more outcomes. The method also includes training a machine learning engine based on the simulated patient population dataset. The machine learning engine generates one or more predicted outcomes based on the training, wherein the machine learning engine generates one or more predicted outcomes based on the training.

BRIEF DESCRIPTION OF THE FIGURES

FIG. 7B illustrates exemplary predicted outcomes generated based on the exemplary query of FIG. 7A.

FIG. 8 illustrates an example of an expert user interface for analyzing an information source via an assisted/supervised natural language processing (NLP) operation.

FIG. 10 illustrates an example expert user interface for generating a patient population source seed.

FIG. 12A illustrates a first exemplary simulated patient population dataset.

FIG. 12B illustrates a second exemplary simulated patient population dataset.

FIG. 14A illustrates an exemplary outcome and feature relationship interface relating a positive lung cancer diagnosis outcome to various feature parameters, including a focus on an cough feature.

DETAILED DESCRIPTION

A dataset generation system is described that receives feature parameters, each feature parameter identifying possible values for one of a set of features. The dataset generation system receives outcomes corresponding to the feature parameters. The dataset generation system generates a simulated patient population dataset with multiple simulated patient datasets, each simulated patient dataset associated with the outcomes and including feature values falling within the possible values identified by the feature parameters. A dataset analysis system may train a machine learning engine based on the simulated patient population dataset and optionally additional simulated patient population datasets. The machine learning engine generates predicted outcomes based on the training in response to queries identifying feature values.

Figure 1:
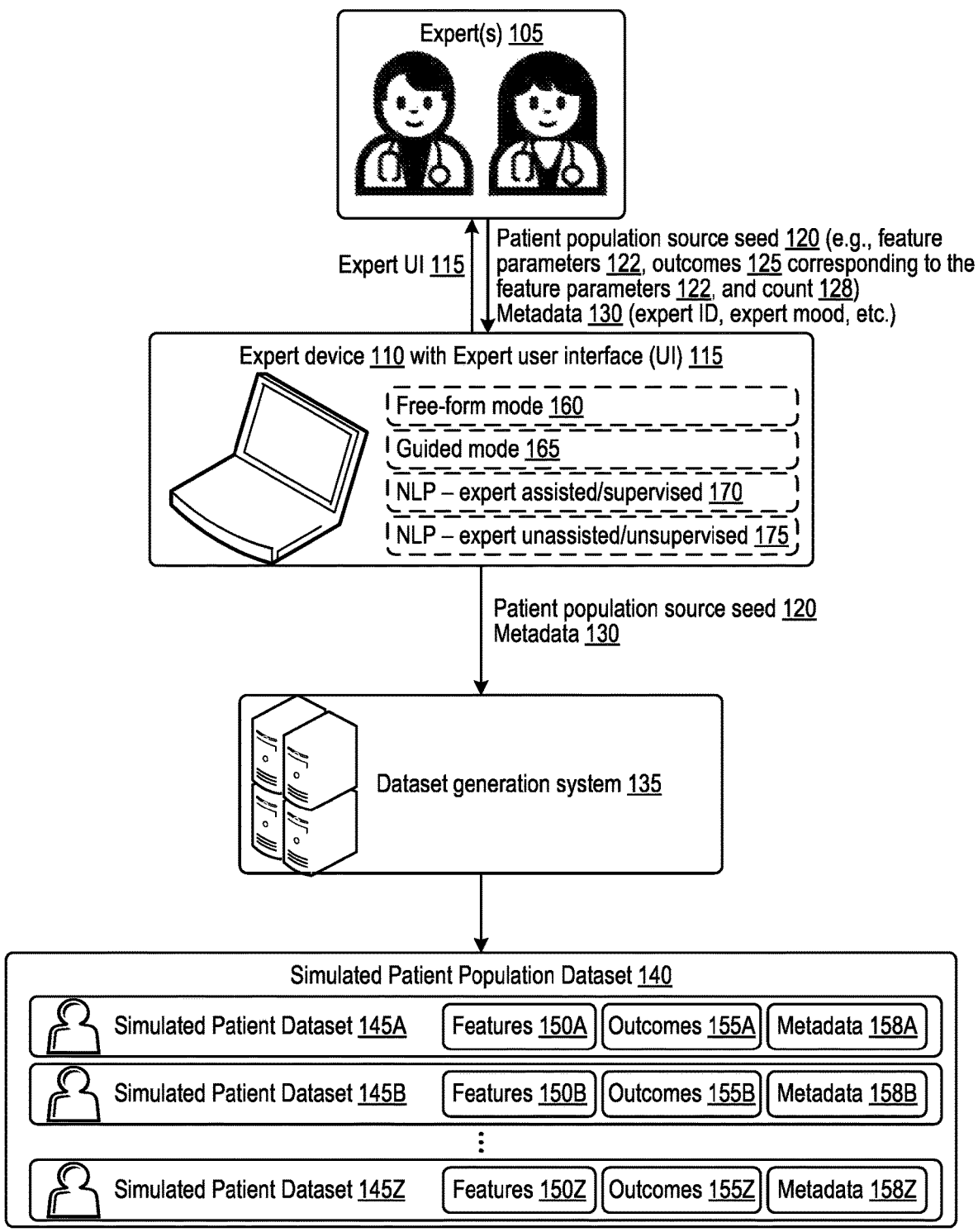
FIG. 1 is a block diagram illustrating generation of a simulated patient population dataset based on a patient population source seed and on expert-provided outcomes.

FIG. 1 is a block diagram illustrating generation of a simulated patient population dataset based on a patient population source seed and on expert-provided outcomes.

The block diagram 100 of FIG. 1 includes an expert device 110 and a dataset generation system 135. One or more experts 105 interact with the expert device 110 through an expert user interface (UI) 115, providing various input data to the expert device 110 through the expert UI 115. The input data may include a patient population source seed 120 and optionally metadata 130. The expert device 110 passes the patient population source seed 120 and optionally metadata 130 on to the dataset generation system 135, which generates a simulated patient population dataset 140 based on the patient population source seed 120 and optionally on the metadata 130. The simulated patient population dataset 140 includes multiple simulated patient datasets 145A-Z that each correspond to a simulated patient. The patient population source seed 120 identifies feature parameters 122, which are discussed further below, and outcomes 125. All of the simulated patient datasets 145A-Z within the simulated patient population dataset 140 are associated with the same outcomes 125—that is, the outcomes 155A-Z are the outcomes 125, for each of the simulated patient datasets 145A-Z within the simulated patient population dataset 140. The feature parameters 122 then provide information about feature values that correspond to those outcomes 125, as discussed further below. If the expert 105 wishes to describe a different set of outcomes than the outcomes 125, the expert then inputs a different patient population source seed with that different set of outcomes, and a separate simulated patient population dataset based on that different set of outcomes is generated by the dataset generation system 135 based on the different patient population source seed.

Each simulated patient dataset of the simulated patient datasets 145A-Z includes features and outcomes that are based on the patient population source seed 120 as discussed further below. Each simulated patient dataset of the simulated patient datasets 145A-Z also includes metadata, which may provide information about the patient population source seed 120, the expert that provided the patient population source seed 120, the resulting simulated patient population dataset 140, or combinations thereof, as discussed further. While the metadata 158A-Z is illustrated separately from the features 150A-Z and the outcomes 155A-Z in FIG. 1, in some cases the metadata 158A-Z may be included in the features 150A-Z. For example, a first simulated patient dataset 145A includes a first set of features 150A, a first set of outcomes 155A, and a first set of metadata 158A; a second simulated patient dataset 145B includes a second set of features 150B, a second set of outcomes 155B, and a second set of metadata 158B; and an $N^{th}$ (e.g., twenty-sixth) simulated patient dataset 145Z includes an $N^{th}$ set of features 150Z, an $N^{th}$ set of outcomes 155Z, and an $N^{th}$ set of metadata 158Z.

The patient population source seed 120 may include one or more feature parameters 122 associated with one or more features. As discussed in further detail below, features may include a patient's physical characteristics, health data, biometric data, medical history, vital signs, symptoms, other signs, test results, and the like. Patient data for a particular patient, whether the patient is real or simulated, may have feature values associated with each feature. These feature values may include numeric values, Boolean true/false values, multiple-choice (e.g., multiple categories) values, string values, Likert scale responses, or combinations thereof. For example, patient data for a particular simulated patient dataset may identify the patient's height as a feature, and may identify that this simulated patient has a numerical feature value of six feet and three inches (i.e., 75 inches or 6.25 feet) for the height feature. Patient data for a particular patient may identify the patient's gender as a feature, with a corresponding boolean gender feature value such as "male" or "female," or a corresponding multiple-choice (AKA "category") feature value selected from multiple possible values such as "male," "female," "other," "decline to state," or "not available (NA)."

Feature parameters 122 in the patient population seed 120 provided to the expert device 110 by an expert 105 through the expert UI 115 may identify one or more possible feature values associated with each feature of one or more features. Each the feature values for the features 150A-Z of the simulated patient population dataset 140 are then generated by the dataset generation system 135 to adhere to the possible feature values identified by the feature parameters 122. An example of an expert UI 115 through which an expert 105 may input a patient population seed 120, including the feature parameters 122 and the outcomes 125 and a count 128, is illustrated in FIG. 10. The one or more possible feature values may in some cases be identified as a range of values, a minimum threshold value, a maximum threshold value, a list of one or more individual possible values, or some combination thereof. For example, the feature parameters 122 may identify that the simulated patient population dataset 140 should be generated to only include simulated patient datasets 145A-Z whose features 150A-Z include ages between 18 and 25, and who are experiencing a cough symptoms that are moderate or greater in severity, who are non-smokers, and who may be male or female.

Figure 13:
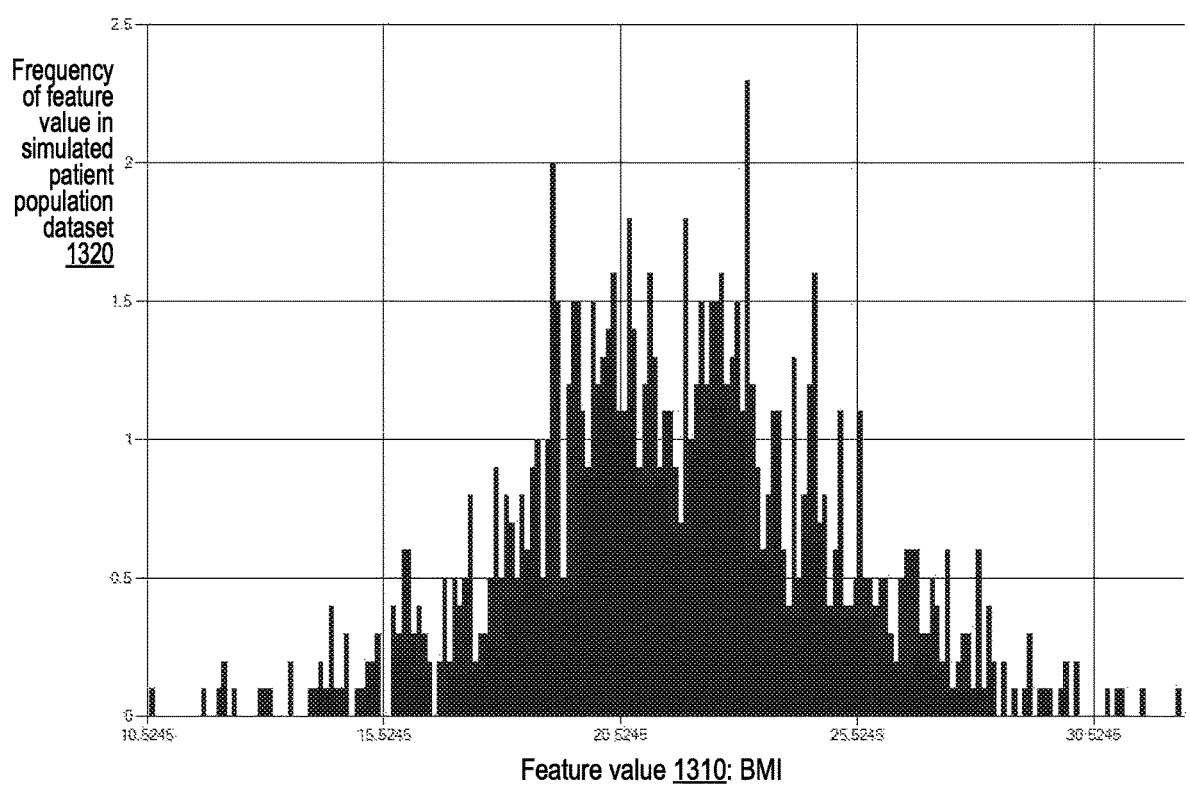
FIG. 13 illustrates an exemplary distribution of feature values for a particular feature within a simulated patient population dataset according to a feature parameter designating a symmetric Gaussian distribution.

The feature parameters 122 may also identify a distribution to be maintained in generating the feature values for features 150A-Z. The feature values may be generated semi-randomly, so that feature values corresponding to a high probability in a distribution (such as the peak of a bell curve) are more likely to be generated than feature values corresponding to a low probability in a distribution (such as the edges of a bell curve). Distributions may include Gaussian distributions (which may also be referred to as "normal" distributions or "bell curves"), asymmetric distributions, linear distributions, polynomial distributions, exponential distributions, logarithmic distributions, power series distributions, sinusoidal distributions, other distributions, or combinations thereof. Distributions may be identified, for example, by mean and standard deviation values, by graph function values, by skew or distortion values, or combinations thereof. For example, the feature parameters 122 may identify that the simulated patient population dataset 140 should be generated to include a Gaussian distribution of feature values for a "patient body mass index (BMI)" feature, with the mean of the BMI feature value being 22 $kg/m^2$ and the standard deviation of the BMI feature value being 3.5 $kg/m^2$. The dataset generation system 135 then generates the BMI feature values for the features 150A-Z semi-randomly, so that the features 150A-Z include a variety of BMI values, but all of the BMI values generated of the features 150A-Z are generated randomly based on probabilities determined according to a Gaussian distribution with identified mean (e.g., 22 $kg/m^2$ as above) and an identified standard deviation (e.g., 3.5 $kg/m^2$ as above) as indicated in the feature parameters 122. An example set of feature values generated based on this example Gaussian BMI distribution is illustrated in FIG. 13 as the distribution 1300.

Distribution functions for feature values may be based on the outcomes 125 and may conform to expected distributions of the feature values within real-world patient populations in which those outcomes 125 are true. An outcome of a diagnosis of lung cancer, for example, may be associated with a particular distribution function for the age feature based on, for example, more than half of lung cancer diagnoses occurring for patients that are 55 to 74 years old, and more than one-third of lung cancer diagnoses occurring for patients that over 75 years of age.

A set of features 150$n$ (where n is a character A-Z) may identify one or more features as well as one or more feature values for each of those features. The set of features 150$n$ may, for example, include features in the form of various types of information about a patient and the patient's circumstances. For example, a set of features 150$n$ may include physical characteristics, such as the patient's gender, age, race, skin color, height, weight, BMI, sex, injuries, physical disabilities, eye color, pupil dilation, ease or difficulty of breathing, functional capacity, gait speed, strength, flexibility, other physical characteristics, or some combination thereof. A set of features 150$n$ may include mental or behavioral characteristics, such as the patient's mental disabilities, delirium, behavioral tics, behaviors, habits, preferences, occupation, relationship/family status, other mental or behavioral characteristics, or some combination thereof. A set of features 150$n$ may include past patient's documentation, insurance information, photos and pictures of patients, patient's family members, and other documentation, or some combination thereof. A set of features 150$n$ may include biometric data, such as pulse, blood pressure, body temperature, breathing rate, oxygen saturation (as measured by pulse oximetry), blood glucose level, heart rate, end-tidal carbon dioxide ($ETCO_2$), other vital signs, other biometric data, or some combination thereof. A set of features 150$n$ may include medical history of the patient or patient's family, such as past or current medical conditions, past or current medications (e.g., with doses and frequencies of administration), past or current surgeries, past or current treatments, past or current allergies, past or current vaccinations, missing (not yet received) vaccinations, other medical history information, or some combination thereof.

A set of features 150n may include symptoms presented by or otherwise detectable from the patient, such as a fever, rash, ache, pain, cough, diarrhea, dysuria, other symptoms, or some combination thereof. Values for the set of features 150n, or the set of features 150n themselves, may in some cases indicate strength or severity level or degree of one or more of the symptoms, such as acute, severe, strong, medium, mild, nonexistent, or some other strength or severity level or degree. A set of features 150n may include test results, such as blood tests, urine tests, medical imaging evaluations, results of a physical examination, other test results, or some combination thereof. A set of features 150n may include the patient's lack of particular organ or body part, such as an amputated limb, an internal organ that has been removed via surgery, an organ that has deteriorated, other lack of particular organ or body part, or some combination thereof. A set of features 150n may include patient activities, such as travel to a foreign country, recreational or work-related activities, job stress, family stress, recent accidents, drug use, exposure to infection, other patient activities, or some combination thereof.

Figure 3:
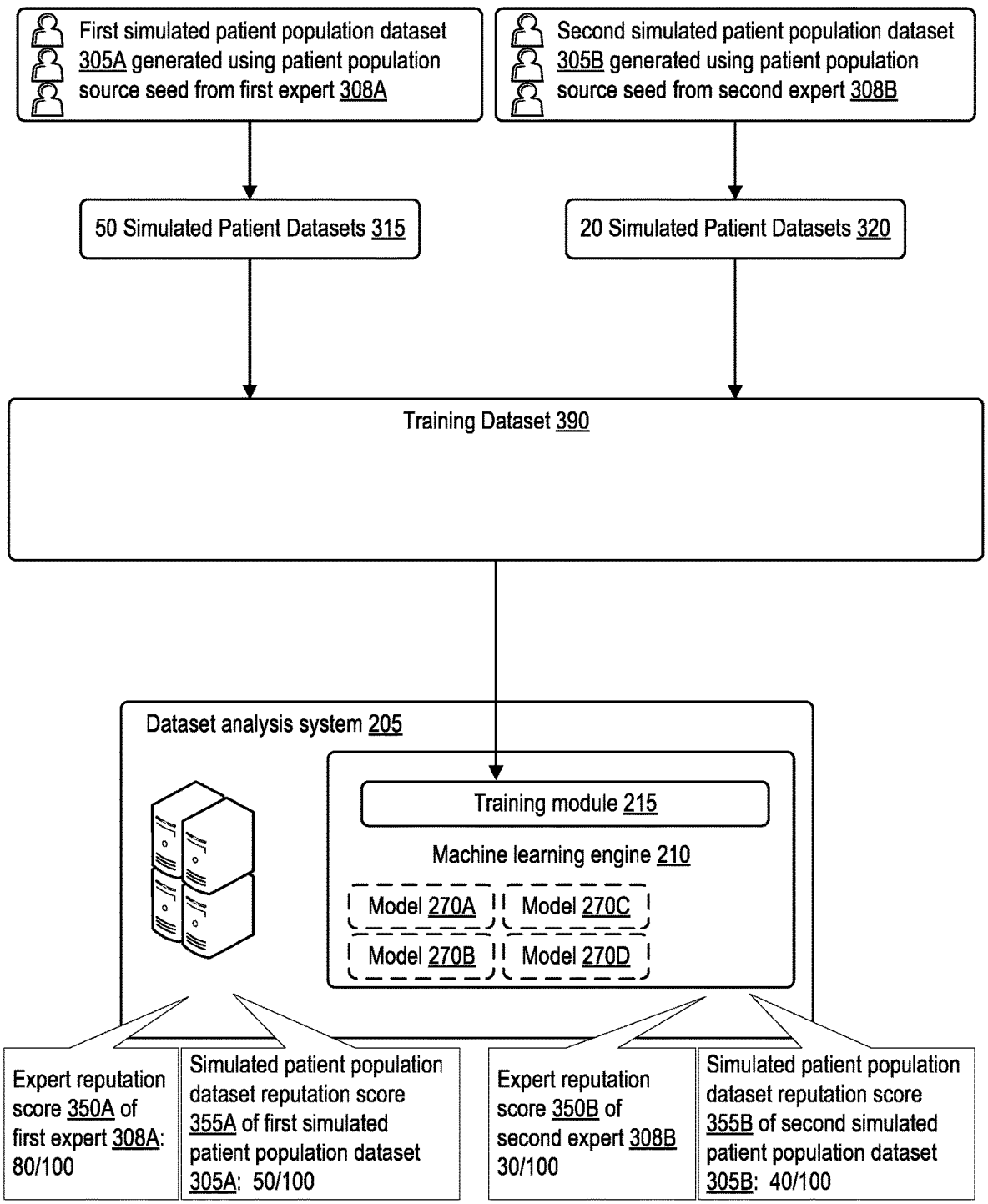
FIG. 3 is a block diagram illustrating scaling of amount of simulated patient datasets used in a training dataset based on reputation scores.

The metadata 158n (where n is a character A-Z) may include the metadata 130 provided to the expert device 110 by the expert 105, by the expert device 110 about the expert 105 and/or about the patient population source seed 120, or otherwise relating to the expert 105, the patient population source seed 120, and/or the resulting simulated patient dataset 140. That is, the metadata 130 may concern an expert 105 or other circumstances relating to gathering the other features or to providing outcomes 155n (where n is a character A-Z). For example, a set of features 150n may include expert identifier (ID) corresponding to the expert 105, an experience level of the expert 105, a mood of the expert 105 during review and analysis of other features to provide outcomes 155n, a time of day during which the expert 105 during reviewed and analyzed other features to provide outcomes 155n, a day of the week during which the expert 105 during reviewed and analyzed other features to provide outcomes 155n, a season during which the expert 105 during reviewed and analyzed other features to provide outcomes 155n, an organization employing the expert 105, an organization to which the expert 105 is a member, an institution providing diagnostic criteria, a device used to generate biometric data or test results, other metadata, or some combination thereof. In some cases, the metadata may in some cases include a reputation score 350$ of the expert (as illustrated in FIG. 3) and a reputation score 355$ of the simulated patient population dataset 140 (as illustrated in FIG. 3), which may added to the metadata 130 and/or be later modified/controlled by the expert device 110, the dataset generation system 135, the dataset analysis system 205, or some combination thereof.

The outcomes 125 of the patient population source seed 120 are provided by the one or more experts 105 via the expert UI 115 and correspond to the patient feature parameters 122. Thus, the outcomes 125 are used as the outcomes 155A-Z for each of the simulated patient datasets 145A-Z of the simulated patient population dataset 140. In some cases, the outcomes 125 may be stored as corresponding to the entire simulated patient population dataset 140. This may use less space than identifying the outcomes 125 for each simulated patient dataset 145A-Z. In the simulated patient population dataset 140 illustrated in FIG. 1, however, the outcomes 125 are stored in each of the simulated patient datasets 145A-Z as the outcomes 155A-Z. While this stores the outcomes 125 in a redundant way while the simulated patient datasets 145A-Z are alone in the simulated patient population dataset 140, this redundancy ensures that the outcomes 125 still identifiably correspond to the simulated patient datasets 145A-Z and their features 150A-Z even if the simulated patient datasets 145A-Z are later moved or merged into a larger database, such as the training dataset 205 of FIG. 2, along with other simulated patient datasets from other simulated patient population datasets associated with other sets of outcomes.

Figure 6:
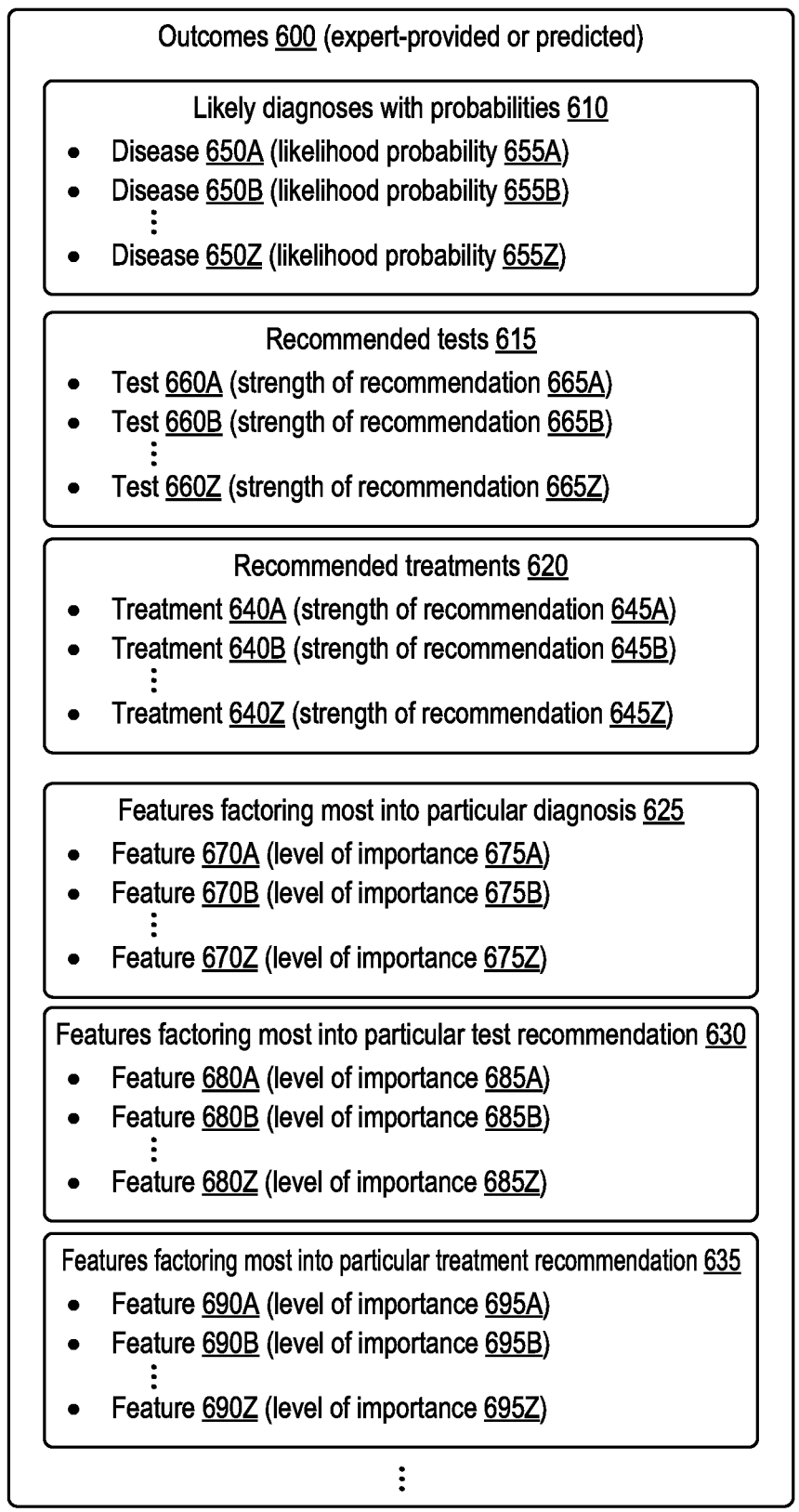
FIG. 6 illustrates a sample format for expert-provided outcomes or predicted outcomes.

The outcomes 125 may include various types of expert input from the one or more experts 105. For example, the outcomes 125 may include likely diagnoses given the feature parameters, optionally along with likelihood probabilities. The outcomes 125 may include recommended tests given the feature parameters, optionally along with strengths of each recommendation. The outcomes 125 may include recommended treatments given the feature parameters, optionally along with strengths of each recommendation. The outcomes 125 may identify features that most factor into one particular diagnosis or other outcome type or another. Examples 1060 of outcomes 125 are illustrated in FIG. 10. While the outcomes 600 and 730 of FIGS. 6 and 7B illustrate predicted outcomes generated by a machine learning engine 210 as discussed further herein, at least some of the types of information shown in the outcomes 600 and 730 may also be present in the outcomes 125.

The patient population source seed 120 may also identify a count 128. The count 128 may identify how many simulated patient datasets 145A-Z should be generated within the simulated patient population 140 by the dataset generation system 135. The count 128 may be a numeric value, such as the value "5,000" shown in the example 1080 of the count 128 illustrated in FIG. 10. In some cases, the count 128 may also identify a distribution, such as the distribution 1300 of FIG. 13.

The simulated patient population dataset 140 may take the form of a table, a database, or a similar data structure. In some cases, each simulated patient dataset may 145n occupy a row in the simulated patient population dataset 140. In such a case, each simulated patient dataset 145n may have a simulated patient identifier uniquely identifying the simulated patient that is being described. A column of the simulated patient population dataset 140 may be dedicated to such simulated patient identifiers, with the cell in that column and in the row of a particular simulated patient dataset 145n including the simulated patient identifier for the simulated patient dataset 145n. In some cases, such simulated patient identifiers may be considered to be one of the features 150n (e.g., as metadata).

Each of the one or more features 150n of the simulated patient dataset 145n may have a column of the simulated patient population dataset 140 dedicated to it. The cells in those columns and in the row corresponding to the simulated patient dataset 145n may then have feature values for each of those features. For example, if the features 150n include age, gender, body temperature, and BMI, then there may be an "age" column, a "gender" column, a "body temperature" column, and a "BMI" column. The cell in the "age" column at the row corresponding to the simulated patient dataset 145n may include a feature value such as 30.6 years. The cell in the "gender" column at the row corresponding to the simulated patient dataset 145n may include a feature value such as male. The cell in the "body temperature" column at the row corresponding to the simulated patient dataset 145n may include a feature value such as 101.4° F. The cell in the "BMI" column at the row corresponding to the simulated patient dataset 145n may include a feature value such as 24.1 kg/m². In some cases, a feature value may be missing for a particular simulated patient dataset 145n and may be marked as "NA," for example. Different types of metadata may also each have dedicated columns, and may optionally be treated as features.

Each of the one or more outcomes 155n of the simulated patient dataset 145n may have a column of the simulated patient population dataset 140 dedicated to it. The cells in those columns and in the row corresponding to the simulated patient dataset 145n may then have outcome values for each of those features. For example, if the outcomes 155n include Chronic Obstructive Pulmonary Disease (COPD), lung cancer, and a recommendation for a pulmonary function test then there may be a "COPD" column, a "lung cancer" column, and a "pulmonary function test" column. The cell in the "COPD" column at the row corresponding to the simulated patient dataset 145n may be binary (true/false) or may include a outcome likelihood value such as 70%. The cell in the "lung cancer" column at the row corresponding to the simulated patient dataset 145n may be binary (true/false) or may include a outcome likelihood value such as 65%. The cell in the "pulmonary function test" column at the row corresponding to the simulated patient dataset 145n may be binary (true/false) or may include a recommendation strength value such as 42%. In some cases, an outcome value may be missing for a particular simulated patient dataset 145n and may be marked as "NA," for example. Examples 1200 and 1250 of simulated patient population datasets 140 are further provided in FIG. 12A and FIG. 12B. Though no simulated patient identifiers or metadata are illustrated in those examples 1200 and 1250, it should be understood that simulated patient identifiers and/or metadata may be present in other simulated patient population datasets.

The expert device 110 and expert UI 115 may include multiple modes of operation, including a free-form mode 160, a guided mode 165, an assisted/supervised natural language processing (NLP) mode 170, and an unassisted/unsupervised natural language processing (NLP) mode 175. Each mode of operation allows for experts 105 to input information identifying of relationships between features' parameters and outcomes and associated creation of one or more simulated patient population datasets based on those features' parameters and outcomes. Each information input session may optionally be identified via a unique input data identifier (ID), which may be itself considered a feature (as metadata). Expert input data may be provided from the expert device 110 to the dataset generation system 135 in many formats, such as HTML, WPF, JSON, XML, YAML, plain text, an encrypted variant of any of these, or a combination thereof. Expert input data may be provided from the expert device 110 to the dataset generation system 135 via an application programming interface (API) or web interface, such as a REST API interface, a SOAP API interface, a different non-REST and non-SOAP API interface, a web interface, or some combination thereof.

In the free-form mode 160, one or more experts 105 provide feature parameters and corresponding outcomes by filling out multiple form fields or other input interfaces manually. The free-form mode 160 may allow the one or more experts 105 to identify a list of features deemed by the one or more experts 105 to be relevant to given outcomes.

In some cases, an expert 105 may not provide feature parameters 122 for certain features through the expert UI 115, in which case feature values for the simulated patient datasets that are generated may have missing "NA" feature values for those missing features. Some machine learning algorithms may sometimes have trouble with missing or "NA" values, in which case the one or more experts 105 may optionally define and/or assign a "default" feature values and/or outcome values when no value is otherwise provided. For example, the expert UI 115 may ask an expert 105 to fill in feature parameters 122 for hundreds of features. The expert 105 may provide feature parameters 122 for important features to a particular outcome or set of outcomes, but may leave blank feature parameters for features that the expert 105 considers irrelevant or does not have enough information about to identify a correlation with the outcome in question. If one of those irrelevant features is age, for example, the expert 105 may select an option to use a default age. The default age may be set to 35, for example. The default age (or any other default feature value) may be set by the expert 105, either during that session or during a previous interact with the expert UI 115. The default age (or any other default feature value) may be set by the expert device 110 and/or by the dataset generation system 135, for example based on an average age or other average feature value as found in the real world, either in general or in relation to the outcomes. The default age (or any other default feature value) may be set based on inputs by one or more other experts 105, optionally for the same outcomes or similar outcomes.

may. For numerical feature and outcome values, a type of distribution may be identified, such as Gaussian distributions, asymmetric distributions, linear distributions, polynomial distributions, exponential distributions, logarithmic distributions, power series distributions, sinusoidal distributions, or combinations thereof. Distributions may be identified based on mean, standard deviation, skew, and so forth, or may be identified based on graph function, or some combination thereof.

Similarly, for categorical (e.g., Boolean or multiple choice) feature values, the one or more experts 105 may, through the free-form mode 160, identify categories/choices and may identify a percentage of prevalence for each category/choice. For example, if the feature in question is "cough," and the available categories are "none," "mild cough," "medium cough," and "severe cough," the one or more experts 105 may specify that 5% of the simulated patient datasets 145A-Z of the simulated patient population dataset 140 will have the "none" value, 20% will have the "mild cough" value, 35% will have the "medium cough" value, and 40% will have the "severe cough" value. The one or more experts 105 may also identify a count of how many simulated patient datasets should be present in the simulated patient population dataset 140. While the letters A-Z imply 26 simulated patient datasets, any number may be selected. Each of the one or more experts 105 may provide, or be assigned, an expert identifier (ID) corresponding to each expert and that expert identifier may be one of metadata 158A-Z included into each simulated patient dataset provided by that expert.

In some cases, different experts may have different expert reputation scores 350, which may be present in the metadata 130. The metadata 158A-Z stored in the simulated patient population dataset 140 may include an expert reputation score 350 of an expert that provided the patient population source seed 120 based upon which the simulated patient population dataset 140 is generated. Alternately, the metadata 158A-Z may store a hyperlink (e.g., URL) or pointer to the expert reputation score, which may be stored in a centralized system such as the dataset generation system 135 and/or the dataset analysis system 205 so that the expert reputation score is consistent across different simulated patient population dataset that are based on patient population source seeds from that user.

Input from a first expert with a high reputation score may be more highly regarded than input from a second expert with a low reputation score that is lower than the high reputation score. The first expert may have a higher reputation score than the second expert based on the first expert having obtained a higher level of education, or a more relevant education, or having had more relevant experience (e.g., as a doctor or other medical professional) than the second expert. A reputation score of an expert may also be raised whenever an expert's provided outcomes agree with outcomes of one or more other experts, especially if the other experts also have high reputation scores. A reputation score of an expert may be reduced whenever an expert's provided outcomes are different from outcomes of one or more other experts.

Additionally, each simulated patient population dataset 140 may have its own simulated patient population dataset reputation score, which may also be stored in the metadata 158A-Z. Alternately, the metadata 158A-Z may include a store a hyperlink (e.g., URL) or pointer to the simulated patient population dataset reputation score, which may be stored in a centralized system such as the dataset generation system 135 and/or the dataset analysis system 205 to maintain consistency. A simulated patient population dataset with a high simulated patient population dataset reputation score may initially be based on the expert reputation score, but may be increased and decreased independently based on validation (as in FIG. 4) and querying user feedback 550 (as in FIG. 5). Expert reputation scores and simulated patient population dataset reputation scores are discussed further with respect to FIGS. 2, 3, and 5.

Figure 5:
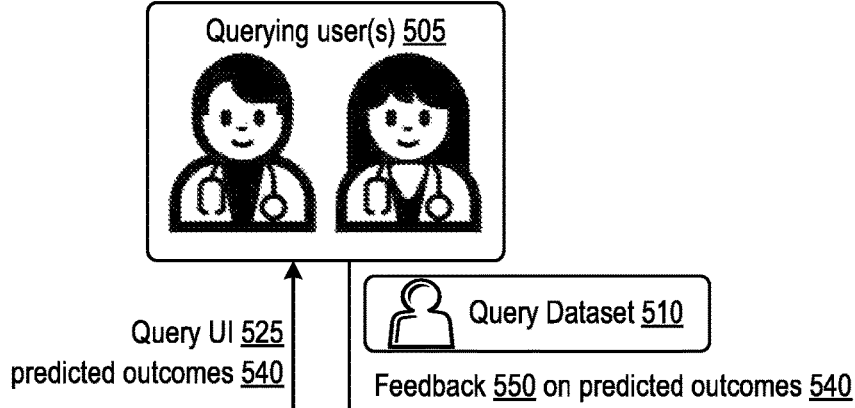
FIG. 5 is a block diagram illustrating generation of predicted outcomes based on a query.

In the guided mode 165, the training module 215 and/or expert UI 115 can provide feedback to the one or more experts 105 inputting data via the expert UI 115, for example by asking questions to one of the experts 105, optionally starting with broader questions and then getting to narrower question. In some cases, the guided mode 165 may be triggered in response to receipt of a query dataset 510 at the query module 425 as illustrated in FIG. 5 and/or negative feedback 550 from querying user Examples of query-triggered and feedback 550-trigerred guided mode 165 are discussed further with respect to FIG. 5.

In the NLP modes 170 and 175, an information source may be provided to (e.g., uploaded to) or identified to (e.g., through a URL or other link) the expert device 110 through the expert UI 115. The information source may be, for example, a document, a website, a publication, or a medical book. The information source may be parsed at the expert device 110 and/or at the dataset generation system 135, which may identify features and corresponding outcomes from the parsed information source. In the assisted/supervised NLP mode 170, one or more experts 105 may assist or supervise the NLP algorithm to ensure that correct correlations between features and outcomes are parsed, and that feature data and/or outcome data is modified if necessary. In the unassisted/unsupervised NLP mode 175, the one or more experts 105 do not assist or supervise the NLP algorithm. An example 800 of an expert UI 115 for analyzing an information source 810 via the assisted/supervised NLP mode 170 is illustrated in FIG. 8.

Figure 15:
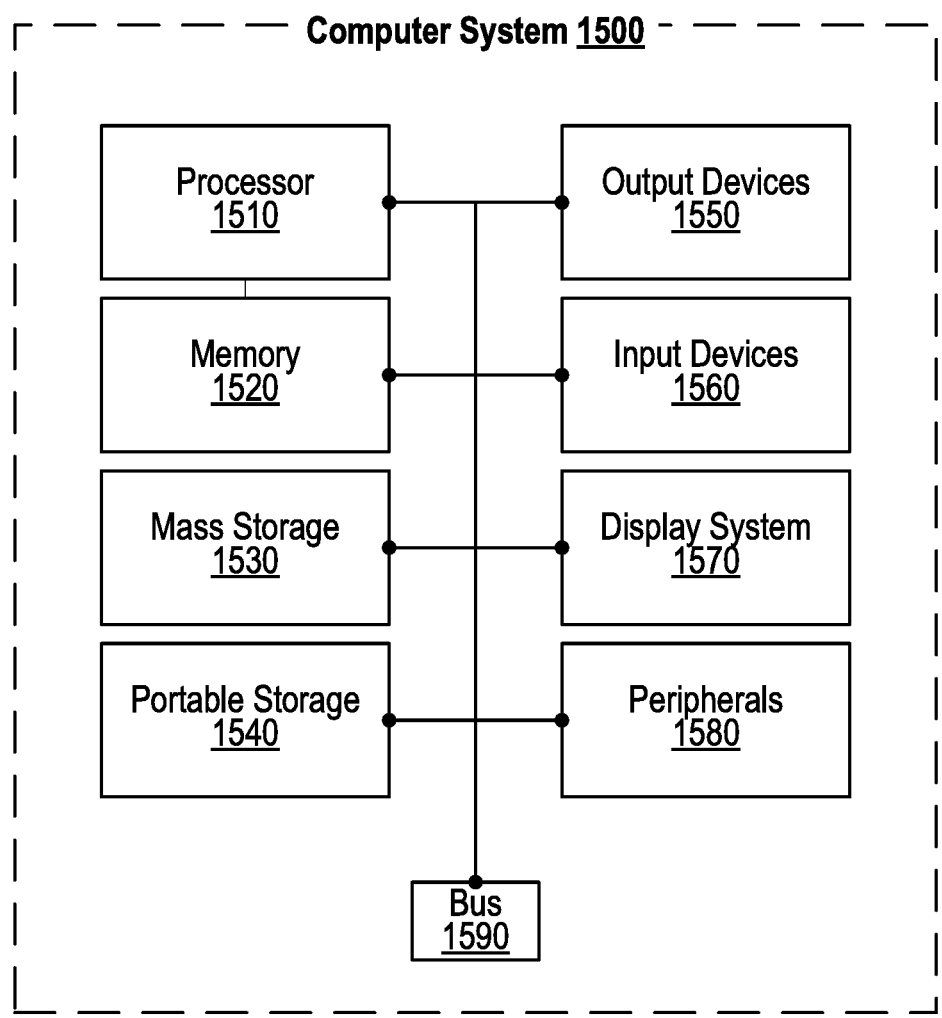
FIG. 15 is a block diagram of an exemplary computing device that may be used to implement some aspects of the technology.

The expert device 110 and/or the dataset generation system 135 may each include one or more computing devices 1500 as illustrated in FIG. 15 and as discussed with respect to FIG. 15. In some cases, the expert device 110 and/or the dataset generation system 135 may include a subset of the components of the computing device 1500 illustrated in FIG. 15 and/or as discussed with respect to FIG. 15. While the expert device 110 and the dataset generation system 135 are illustrated as separate computing devices and/or separate sets of computing devices in FIG. 1, in some cases the expert device 110 and the dataset generation system 135 may be co-located on a single set of one or more computing devices 1500, or may share one or more computing devices 1500 in common. In some cases, the dataset generation system may be alternately referred to as a dataset generation module, a dataset generation device, a patient simulation system, a patient simulation module, or a patient simulation device.

Figure 2:
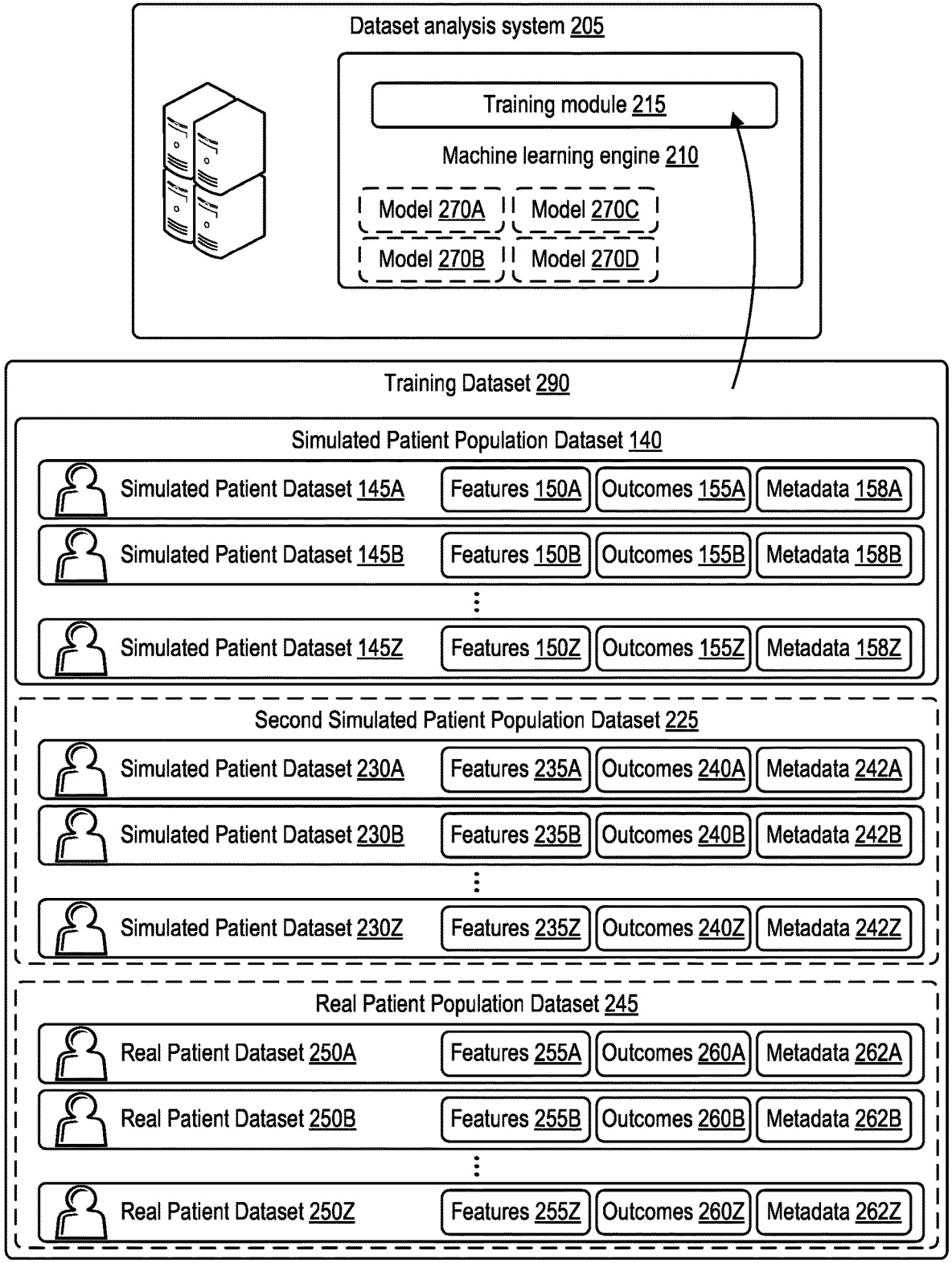
FIG. 2 is a block diagram illustrating training of a machine learning engine of a dataset analysis system based on at least one simulated patient population dataset.

FIG. 2 is a block diagram illustrating training of a machine learning engine of a dataset analysis system based on at least one simulated patient population dataset.

A training dataset 290 may be generated by the dataset generation system 135 and/or by a dataset analysis system 205. The training dataset 290 may be generated to include at least a subset of the simulated patient population dataset 140—that is, the training dataset 290 may include one or more of the simulated patient datasets 145A-Z of the simulated patient population dataset 140. How many of the simulated patient datasets 145A-Z are included in the training dataset 290 may be based on the count 128 associated with the simulated patient population dataset 140, on the simulated patient population dataset reputation score associated with the simulated patient population dataset 140, on the expert reputation score associated with the expert 105 that provided the patient population source seed 120 based upon which the simulated patient population dataset 140 was generated, one or more characteristics of the machine learning engine 210 (e.g., size of training datasets that it is capable of receiving as input), or some combination thereof.

The training dataset 290 may be generated to include at least a subset of a second simulated patient population dataset 225 as well, similarly based on counts and/or second simulated patient population dataset reputation score and/or expert reputation and/or characteristics of the machine learning engine 210. The training dataset 290 may be generated to include at least a subset of a third simulated patient population dataset (not pictured), at least a subset of a fourth simulated patient population dataset (not pictured), and so forth—any number of simulated patient population datasets, or subsets thereof, may be included in the training dataset 290. The training dataset 290 may be generated to include at least a subset of a real patient population dataset 245 as well, which may likewise be based on a count of real patient datasets 250A-Z included within the real patient population dataset 245, a real patient population dataset reputation score, an expert reputation score of an expert that provided the real patient population dataset 245, and/or characteristics of the machine learning engine 210. The training dataset 290 may be generated to include at least a subset of a second real patient population dataset (not pictured), at least a subset of a third real patient population dataset (not pictured), at least a subset of a fourth real patient population dataset (not pictured), and so forth—any number of real patient population datasets, or subsets thereof, may be included in the training dataset 290. The training dataset 290, which includes at least a subset of the simulated patient population dataset 140 generated by the dataset generation system 135 of FIG. 1 as discussed above, is input into a training module 215 of a machine learning engine 210 of a dataset analysis system 205 in FIG. 2. In some cases, the training dataset 290 may be referred to as the knowledge dataset, the knowledge base, the knowledge database, the training information, the training base, the training database, or some combination thereof.

The second simulated patient population dataset 225 is illustrated in FIG. 2 as also optionally being a part of the training dataset 290 that is input into the training module 215 to train the machine learning engine 210 of the dataset analysis system 205. The second simulated patient population dataset 225 includes multiple simulated patient datasets 230A-Z, each including features, metadata, and outcomes identified as features 235A-Z, outcomes 240A-Z, and metadata 242A-Z, respectively. The second simulated patient population dataset 225 may concern different outcomes and/or features and/or metadata than the simulated patient population dataset 140.

A real (not simulated) patient population dataset 245 is also illustrated in FIG. 2 as also optionally being input into the training module 215 to train the machine learning engine 210 and thereof all models 270A-Z of the dataset analysis system 205. The real patient population dataset 245 includes multiple real patient datasets 250A-Z, each including features and outcomes identified as features 255A-Z and outcomes 260A-Z respectively. In some cases, more than one simulated patient population dataset may be input into the training module 215 to train the machine learning engine 210 of the dataset analysis system 205.

In some cases, the dataset analysis system 205 may perform feature naming normalization before the training dataset 290 is input into the training module 215. Feature naming normalization may rename features in certain simulated or patient population datasets so that features that should be the same, but are inconsistently named, are modified to be named consistently. For example, one simulated patient population dataset in the training dataset 290 may have a feature titled "age" while another may simulated patient population dataset in the training dataset 290 may have a feature "how old are you?" These clearly refer to the same feature, so feature naming normalization may rename the "how old are you?" feature to "age" or vice versa. In some cases, a simulated patient population dataset 140 may store one or more possible aliases for each feature (or for certain features). For example, the "age" feature may have "ages" or "years" or "how old" or "how old are you?" as possible aliases. If aliases of features across different simulated patient population datasets match, these features may be normalized by renaming one or both feature names so that the features appear consistently named, allowing simulated patient datasets that were originally from different simulated patient population datasets to be easily compared. If there is no alias match, the feature naming normalization process may identify "orphan" features that appear in one simulated patient population dataset but not another, and may ask an expert 105, or a querying user 505, to check if any of these "orphan" features can be renamed to match an existing feature. In some cases, feature naming normalization may occur after training (e.g., in response to input from a querying user 505), in which case the training dataset 290 may be regenerated and training of the machine learning engine 210 using the training dataset 290 may be performed via the training module 215 again.

As noted above, expert reputation score, simulated patient population reputation score, count 218, and characteristics of the machine leaning engine 210 may impact how many simulated patient datasets from a particular simulated patient population dataset are included in the training dataset 290. By default, the training dataset 290 may pull a set amount of simulated patient datasets from a particular simulated patient population dataset, the default amount optionally based on the characteristics (e.g., training capabilities) of the machine leaning engine 210. This default amount may be a percentage, such as 5%, 10%, 15%, 20%, 25%, 30%, 35%, 40%, 45%, 50%, 55%, 60%, 65%, 70%, 75%, 80%, 85%, 90%, 95%, or 100%. This default amount may be a particular number of simulated patient datasets, such as 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000. This default value may optionally be increased by a delta amount, or a multiple of the delta amount, if the corresponding expert reputation score is higher than a reputation score threshold (e.g., an average reputation score) and/or if the corresponding simulated patient population dataset reputation score is higher than a reputation score threshold (e.g., an average reputation score). This default value may optionally be decreased by the delta amount, or a multiple of the delta amount, if the corresponding expert reputation score is lower than a reputation score threshold (e.g., an average reputation score) and/or if the corresponding simulated patient population dataset reputation score is lower than a reputation score threshold (e.g., an average reputation score). The multiple of the delta amount may be used if the reputation scores deviate from the threshold by a large amount. For example, the multiple of the delta amount may be based on how many standard deviations a reputation score is from an average reputation score. If a count 218 is higher or lower than the default amount, this may also increase or decrease the default amount, for example to be equal to the count 218 (e.g., if the count 218 is lower than the default amount) or by the delta or a multiple of the delta (e.g., if the count 218 is higher than the default amount).

In some cases, the expert reputation score and/or the simulated patient population dataset reputation score may be increased or decreased after training, for example based on feedback 550 of a querying user 505 as in FIG. 5. In such situations, the training dataset 290 may optionally be re-generated, with the amount of simulated patient datasets pulled from a simulated patient population dataset optionally modified based on the increase or decrease in the expert reputation score and/or the simulated patient population dataset reputation score. The newly re-generated training dataset 290 may then be input back into the training module 215 to train the machine learning engine 210.

Figure 14B:
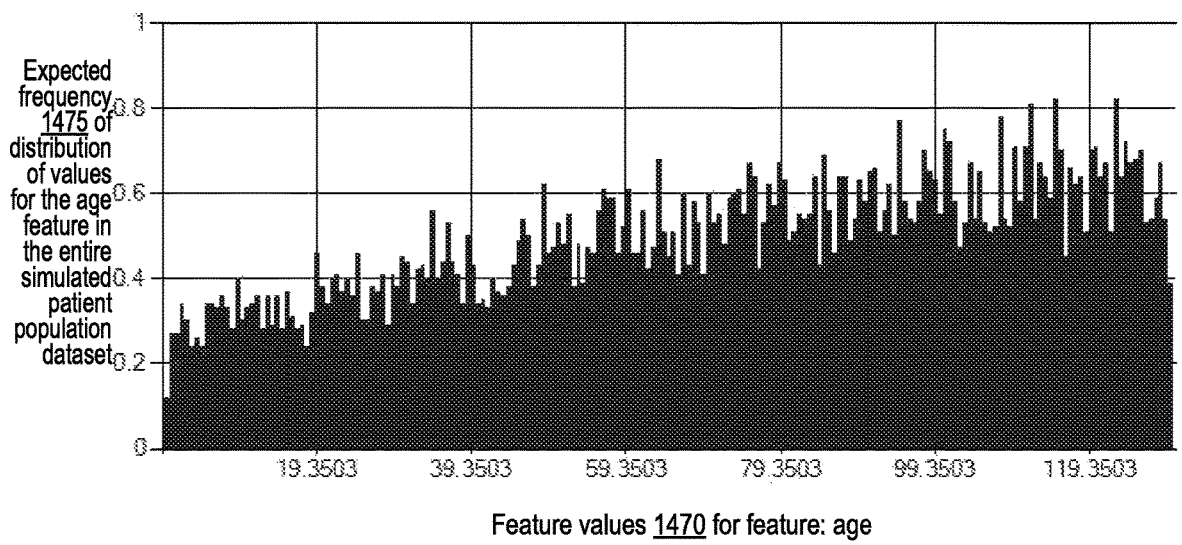
FIG. 14B illustrates an exemplary outcome and feature relationship interface relating a positive lung cancer diagnosis outcome to various feature parameters, including a focus on an age feature.

The machine learning engine 210, once trained based on the training dataset 290 (e.g., the simulated patient population dataset 140 and optionally one or more additional simulated and/or real patient population datasets), may generate one or more artificial intelligence (AI) or machine learning (ML) models that the machine learning engine 210 may use to generate predicted outcomes 540 based on query datasets 510 as discussed further in FIG. 5. Four such models are illustrated in FIG. 2, namely a first model 270A, a second model 270B, a third model 270C, and a fourth model 270D. Some examples of these AI/ML models are illustrated in FIGS. 14A and 14B. In some cases, the models may be generated as decision trees, such as the decision tree 900 of FIG. 9.

To generate the decision trees and/or other types of AI and/or ML models, the machine learning engine 210 may use one or more machine learning algorithms, including a random forest algorithm, a support vector machine (SVM)

algorithm, a gradient boosting machine (GBM) algorithm, a logistic regression algorithm, a linear regression algorithm, a naive Bayes algorithm, a k-Nearest Neighbors (kNN) algorithm, a k-means algorithm, a dimensionality reduction algorithm algorithm, a Markov decision process (MDP) algorithm, a deep learning algorithm, a convolutional neural network (CNN) algorithm, a time delay neural network (TDNN) algorithm, a probabilistic neural network (PNN), other algorithms, or some combination thereof. In some cases, certain decision trees and/or other types of AI/ML models may be input manually by an expert 105 via the expert user interface 115 of the expert device 110. In other cases, one of the above-discussed machine learning algorithms may be used by the machine learning engine 210 to generate a decision tree and/or other type of AI/ML model, which may be shown during or after generation to one or more experts 105 so that the one or more experts 105 can optionally assist with or supervise generation of the decision tree and/or other type of AI/ML model, or modify the decision tree and/or other type of AI/ML model after generation. In other cases, one of the above-discussed machine learning algorithms may be used by the machine learning engine 210 to generate a decision tree and/or other type of AI/ML model, which may be used right away by the machine learning engine 210 to generate predicted outcomes 540 without supervision, assistance, or modification by any experts 105.

In some cases, the AI/ML models may be imported into the machine learning engine 210 (e.g., from another machine learning engine of another data analysis system 205) or exported from the machine learning engine 210 to be imported into another machine learning engine (e.g., allowing a user to sell, trade, or otherwise provide one or more of the AI/ML models to another user).

The dataset analysis system 205 may include one or more computing devices 1500 as illustrated in FIG. 15 and as discussed with respect to FIG. 15. In some cases, the dataset analysis system 205 may include a subset of the components of the computing device 1500 illustrated in FIG. 15 and/or as discussed with respect to FIG. 15. While the dataset analysis system 205 is illustrated as a separate computing device or set of computing devices from the expert device 110, the dataset generation system 135, and the query device 425, in some cases, at least a subset of these systems may be co-located on a set of one or more computing devices, or may share one or more computing devices in common.

FIG. 3 is a block diagram illustrating scaling of amount of simulated patient datasets used in a training dataset based on reputation scores.

A training dataset 390, which may be an example of a training set 290 of FIG. 2, is illustrated being input into the training module 215 to train the machine learning engine 210. The training dataset 390 may be generated by the dataset analysis system 205, by the dataset generation system 135, or some combination thereof. The training dataset 390 includes a set 315 of fifty simulated patient datasets from a first simulated patient population dataset 305A generated using patient population source seed from first expert 308A, and a set 320 of twenty simulated patient datasets from a second simulated patient population dataset 305B generated using patient population source seed from second expert 308B. This discrepancy (fifty vs. twenty) may be based on reputation scores as discussed previously.

The dataset analysis system 205 analyzes the metadata stored in the first simulated patient population dataset 305A to identify an expert reputation 350A of the first expert 308A, which is identified as a high 80 out of a possible 100, and to identify a simulated patient population dataset reputation score 355A of the first simulated patient population dataset 305A, which is identified as a medium 60 out of a possible 100. The dataset analysis system 205 analyzes the metadata stored in the second simulated patient population dataset 305B to identify an expert reputation 350B of the second expert 308B, which is identified as a low 30 out of a possible 100, and to identify a simulated patient population dataset reputation score 355B of the second simulated patient population dataset 305B, which is identified as a low 40 out of a possible 100. These analyses may alternately be performed by the dataset generation system 135 in some cases. The training dataset 390 thus draws a smaller set 320 of twenty simulated patient datasets from the second simulated patient population dataset 305B and a larger set 315 of fifty simulated patient datasets from the first simulated patient population dataset 305A based on the high reputation scores 350A and 355A, and based on the low reputation scores 350B and 355B. In some cases, where both expert reputation scores 350 and simulated patient population dataset reputation scores 355 are used, they may be averaged together for easier comparison between different simulated patient population datasets.

Figure 4:
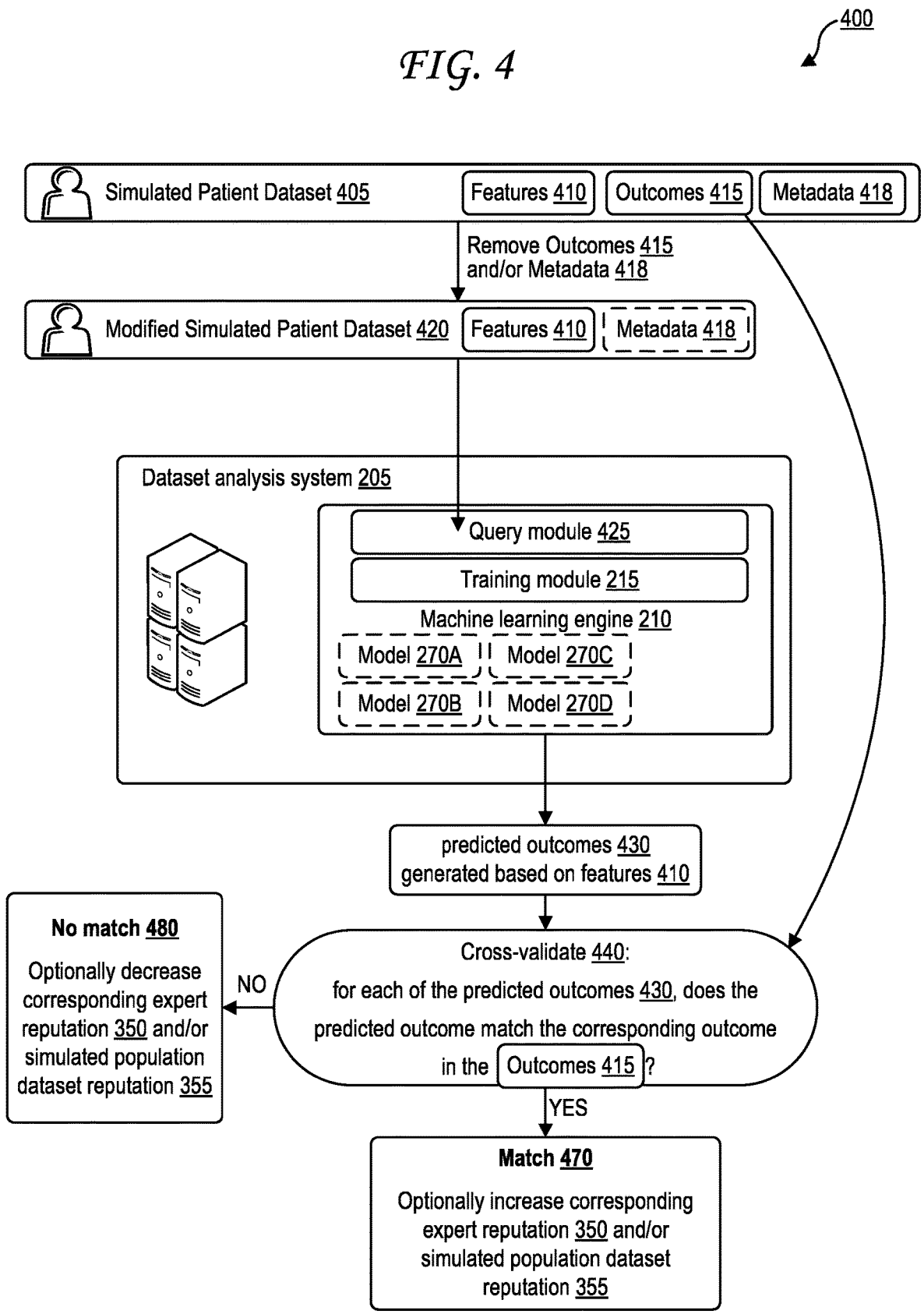
FIG. 4 is a block diagram illustrating cross-validation of predicted outcomes generated using the machine learning engine against expert-provided outcomes.

FIG. 4 is a block diagram illustrating cross-validation of predicted outcomes generated using the machine learning engine against expert-provided outcomes.

During the cross-validation process 400 of FIG. 4, a simulated patient dataset 405 is pulled from a simulated patient population dataset. The simulated patient dataset 405 includes features 410, outcomes 415, and metadata 418. The simulated patient dataset 405 is modified via removal of the outcomes 415 and optionally the metadata 418 to become the modified simulated patient dataset 420 that includes the features 410 and optionally the metadata 418 without the outcomes 415. The modified simulated patient dataset 420 then behaves like a query dataset 510. The modified simulated patient dataset 420 is input into a query module 425 of the machine learning engine 210, similarly to how the query dataset 510 is in FIG. 5. The machine learning engine 210 identifies the features 410 and their corresponding feature values and queries the various models 270A-D to generate one or more predicted outcomes 430 based on the features 410.

Cross-validation 440 is then performed, optionally by the dataset analysis system 205 and/or by another system not pictured. During cross-validation 440, each predicted outcome of the one or more predicted outcomes 430 is compared with the outcomes 415 that were originally in the simulated patient dataset 405. If one of the predicted outcomes 430 matches one of the outcomes 415, then that predicted outcome 430 is identified as a match 470. Optionally, in the event of a match 470, the dataset analysis system 205 may increase an expert reputation score 350 of the expert that provided the patient population source seed 120 for the simulated patient population dataset from which the simulated patient dataset 405 is drawn. Optionally, in the event of a match 470, the dataset analysis system 205 may increase a simulated patient population score 355 of the simulated patient population dataset from which the simulated patient dataset 405 is drawn.

If one of the predicted outcomes 430 does not match any of the outcomes 415, then that predicted outcome is identified as no match 480. Optionally, in the event of no match 480, the dataset analysis system 205 may decrease an expert reputation score 350 of the expert that provided the patient population source seed 120 for the simulated patient population dataset from which the simulated patient dataset 405 is drawn. Optionally, in the event of a match 470, the dataset analysis system 205 may decrease a simulated patient population score 355 of the simulated patient population dataset from which the simulated patient dataset 405 is drawn. As discussed above, any increases or decreases in these reputation scores 350/355 may result in re-generation of the training dataset 290 and re-training of the machine learning engine 210 via the re-generated training dataset.

Incorrect matches may refer both to outcomes and corresponding probabilities or recommendation strength values. For example, if the predicted outcomes 430 include an outcome indicating "lung cancer" and a probability of 40%, while the outcomes 415 include an outcome indicating "lung cancer" and a probability of 70%, then the training module 215 may tune or modify one or more of the models so that the features 410, if present again in a query dataset 510, will output in resulting predicted outcomes 540 an outcome indicating "lung cancer" and a probability of 70% (not 40%). Similarly, if the predicted outcomes 430 include an outcome indicating "pulmonary function test" and a recommendation strength of 20%, while the outcomes 415 include an outcome indicating "pulmonary function test" and a recommendation strength of 42%, then the training module 215 may tune or modify one or more of the models so that the features 410, if present again in a query dataset 510, will output in resulting predicted outcomes 540 an outcome indicating "pulmonary function test" and a recommendation strength of 42% (not 20%).

If the predicted outcomes 430 are missing a particular outcome present in the outcomes 415, the then the training module 215 may tune or modify one or more of the models so that the features 410, if present again in a query dataset 510, will output in resulting predicted outcomes 540 that particular outcome with the outcome value present in the outcomes 415. It may do so, in some cases, by re-generating the training dataset 290 after modifying which simulated patient datasets are included in the training dataset 290, so ensure that simulated patient datasets with the missing outcome are included. The experts 105 may be asked via the expert user interface 115 to provide a new patient population source seed 120 for a new simulated patient population dataset with the missing outcome included if none exist. If the predicted outcomes 430 include an additional outcome that is missing from the outcomes 415, the then the training module 215 may tune or modify one or more of the models so that the features 410, if present again in a query dataset 510, will not output the additional outcome in the resulting predicted outcomes 540.

While the cross-validation operations 400 are only illustrated for a single simulated patient dataset 405, it should be understood that the cross-validation operations 400 may be repeated for any number of simulated patient datasets 405 in a simulated patient population dataset, or in a training dataset 290 with multiple simulated patient population datasets. In some cases, the modified simulated patient dataset 420 and/or outcomes 415 are provided by an expert 105 before and/or during cross-validation operations 400 rather than being pulled from existing simulated patient population dataset(s).

The cross-validation operations 400, and re-generation of the training dataset 290 to change included simulated patient datasets, may in some cases be used to tune the machine learning engine 210 to reduce false positives and false negatives in the predicted outcomes. A false positive in the context of the machine learning engine 210 may include an outcome indicating that a particular diagnosis is likely when that diagnosis should not be likely. A false positive may also include an outcome recommending a test or treatment that should not be recommended, or more strongly than the test or treatment should be recommended. A false negative in the context of the machine learning engine 210 may include an outcome not mentioning a particular diagnosis at all, or mentioning that the diagnosis is unlikely, when that diagnosis should be likely. A false negative may also include an outcome not recommending a test or treatment that should be recommended, or weakly recommending a test or treatment that should be recommended more strongly. Reducing the rate of false positives and/or of false negatives may be identified by an increase in area under a receiver operating characteristic (ROC) curve (AUC) associated with the machine learning engine 210, as greater AUC denotes greater accuracy in classification.

FIG. 5 is a block diagram illustrating generation of predicted outcomes based on a query.

The block diagram 500 of FIG. 5 includes a query device 520 and the dataset analysis system 205. One or more querying users 505 interact with the query device 520 through a query user interface (UI) 525, providing a query dataset 510 to the query device 520 through a query user interface (UI) 525. The query dataset 510 may identify one or more features and one or more feature values for those features, as in the example query dataset 710 of FIG. 7A. The query device 110 may then send the query dataset 510 to the query module 420 of the machine learning engine 210 of the dataset analysis system 205. The query module 420 queries the various models 270A-D of the machine learning engine 210. Each model of the models 270A-D may be tailored to a particular outcome (e.g., particular diagnosis, recommended test, recommended treatment, etc.). Therefore, each model, when queried with the features from the query dataset 510, identifies whether the outcome that the model is tailored to is a predicted outcome or not. In this way, the machine learning engine 210 generates a set of one or more predicted outcomes 540 based on the query dataset 510. An example format for the one or more predicted outcomes 540 is illustrated in FIG. 6.

The one or more predicted outcomes 540 are provided from the dataset analysis system 205 to the query device 520. Upon receipt of the one or more predicted outcomes 540, the query device 520 renders and displays the one or more predicted outcomes 540 for the one or more querying users 505 to review, optionally through the query UI 525. In some cases, the one or more querying users 505 may input feedback 550 about the one or more predicted outcomes 540 into the query device 520 upon reviewing the one or more predicted outcomes 540, optionally through the query UI 525. The feedback 550 may include feedback for the entire set of one or more predicted outcomes 540. The feedback 550 may include feedback for each predicted outcome of the set of one or more predicted outcomes 540.

If the feedback 550 for one or more of the predicted outcome 540 is positive, the training dataset 290 and any models 270A-D that were produced based on training from the training dataset 290 may be maintained as-is. In some cases, positive feedback 550 on the predicted outcomes 540 may increase one or more expert reputation scores 350 of one or more experts, if the models 270A-D that generated the predicted outcomes 540 were based on one or more simulated patient population datasets whose patient population source seeds were provided by those experts. In some cases, positive feedback 550 on the predicted outcomes 540 may increase one or more simulated patient population dataset reputation scores 355 of one or more simulated patient population datasets, if the models 270A-D that generated the predicted outcomes 540 were based on the one or more simulated patient population datasets. If reputation scores 350 and/or 355 are increased, the training dataset 290 may be re-generated as discussed above, as amounts of simulated patient datasets included within the training dataset 290 from simulated patient population datasets may be modified.

If the feedback 550 for one or more of the predicted outcome 540 is negative, the training dataset 290 and any models 270A-D that were produced based on training from the training dataset 290 may be re-tuned and re-generated. In some cases, negative feedback 550 on the predicted outcomes 540 may decrease one or more expert reputation scores 350 of one or more experts, if the models 270A-D that generated the predicted outcomes 540 were based on one or more simulated patient population datasets whose patient population source seeds were provided by those experts. In some cases, negative feedback 550 on the predicted outcomes 540 may decrease one or more simulated patient population dataset reputation scores 355 of one or more simulated patient population datasets, if the models 270A-D that generated the predicted outcomes 540 were based on the one or more simulated patient population datasets. If reputation scores 350 and/or 355 are decreased, the training dataset 290 may be re-generated as discussed above, as amounts of simulated patient datasets included within the training dataset 290 from simulated patient population datasets may be modified.

Considerable technical benefits are provided by generating a simulated patient population dataset 140 as illustrated in FIG. 1, using the simulated patient population dataset 140 to train a machine learning engine 210 as illustrated in FIG. 2, and using the trained machine learning engine 210 to provide predicted outcomes 540 in response to queries 510 as in FIG. 5. For example, system security and privacy are improved, as no real patient data is put at risk. Quantity and quality of training data may be improved, as the simulated patient population dataset 140 can generate thousands or millions of simulated patient datasets matching particular feature parameters, even if some of those feature parameters are very rare or uncommon in real world patients. This improvement to quantity and quality of training data also brings an improvement in accuracy and confidence, as the machine learning engine 210 is able to output a predicted outcome with high confidence even in response to a query that requests a predicted outcome based on rare or uncommon symptoms and/or other features. This is especially important for rare outcomes. For example, generating of a simulated patient population dataset, generated by methods herein explained, for an outcome of a presence of Goodpasture syndrome, a rare disease affecting about one in every million people, is the only way to obtain accurate and dependable training dataset for machine learning models on Goodpasture syndrome. The incidence of this disease in real patient records and electronic medical health records is so low that it approaches data noise levels. In other words, the chances of error, for example of human data entry error (e.g., during entering diagnosis code into patient records), or laboratory error when measuring the anti-GBM antibody levels (diagnostic test for the disease) by mislabeling patient's specimen, or misdiagnosis, and such, are so high, that machine learning algorithms may be unable to train effectively on such rare outcomes with real patient data alone.

System flexibility and expandability is also improved, as the machine learning engine 210 can be quickly trained with new outcomes (e.g., newly discovered diseases or treatments) when such new outcomes become available (e.g., through discovery of the new disease or treatment), and can be quickly trained to recognize new features (e.g., new symptoms, behaviors) when such new features are available, simply by generating new simulated patient population dataset(s) based on the new outcomes and/or the new features and inputting the new simulated patient population dataset(s) into the training module 215 to train the machine learning engine 210.

Quality and verifiability of predicted outcomes may also be improved, as multiple experts 105 may independently provide multiple outcomes 125 for the simulated patient population datasets. Cross-verification 400 as illustrated in FIG. 4, and feedback 550 as illustrated in FIG. 5, may modify reputation scores 350/355, causing re-generation of the training dataset 290 as discussed with respect to at least FIGS. 1, 2, and 3. This improves quality and verifiability.

Returning to a discussion of the guided mode 165 of the expert device 110 of FIG. 1, sometimes receipt of a query dataset 510 at the query module 425 may trigger the expert UI 115 request information from one or more experts in the guided mode 165. For example, the guided mode 165 may be triggered if the machine learning engine 210 is having trouble distinguishing between two predicted outcomes 540. For example, the two most likely diagnoses in the exemplary predicted outcomes 730 of FIG. 7B have very similar likelihoods: chronic obstructive pulmonary disease (COPD) with a likelihood of 70% and lung cancer with a likelihood of 69%. The machine learning engine 210 may understand, based on input data identifiers and/or similarity in associated features and/or feature values, that COPD and lung cancer are both pulmonary diseases and are both potentially life-threatening. However, since both are being output at similar likelihoods, and both require different treatments, such predicted outcomes 540 are a suboptimal results for the querying user In such a case, the guided mode 165 may request information from the one or more experts 105 via the expert UI 115 of the expert device(s) 110. In the guided mode 165, the expert UI 115 may first ask the one or more experts 105 about their level of familiarity/experience with COPD and with lung cancer. If an expert 105 responds highly (e.g., above a predetermined threshold) to both, the expert UI 115 in the guided mode 165 may indicate to the expert 105, for example:

> Machine learning engine 210 sometimes has difficulty distinguishing efficiently between lung cancer and chronic obstructive pulmonary disease (COPD). The 5 most important features, or clinical findings, for the presence of lung cancer, as determined by the machine learning engine 210 are: history (or no history) of smoking, presence (or not) of heavy cough, having (or not) normal of chest×ray, gender, and having (or not) family history of lung cancer and patient's age (total 5). The 5 most important features, or clinical findings, for the presence of chronic obstructive pulmonary disease (COPD), as determined by the machine learning engine 210 are: presence (or not) of heavy cough, having (or not) normal chest x ray, history (or no history) of smoking, age, and gender. Can you think of one more feature besides those listed above, or other predictor such as a diagnostic test or finding on a physical examination or medical history, that can further differentiate between COPD and lung cancer?

In response to receiving an answer to this question from the expert 105 that identifies another feature or predictor, the expert UI 115 in the guided mode 165 may interact with the dataset generation system 135 to automatically generate a new patient population source seed for a new simulated patient population dataset based on the feature or predictor in the answer. For example, the expert 105 may answer by identifying a test to undergo, namely "chest CT scan." The guided mode 165 may request information as to possible feature values or categories for the feature "chest CT scan" if they do not already exist, and their associations with COPD and/or lung cancer. The expert 105 may answer that 90% of patients with lung cancer correspond to a feature value "positive for mass, tumor, or other findings suggesting lung cancer" for the "chest CT scan" feature, and that 10% of patients with lung cancer correspond to a feature value "negative for findings typical for lung cancer" for the "chest CT scan" feature. The expert 105 may answer that 10% of patients with COPD correspond to the feature value "positive for mass, tumor, or other findings suggesting lung cancer" for the "chest CT scan" feature, and that 90% of patients with COPD cancer correspond to the feature value "negative for findings typical for lung cancer" for the "chest CT scan" feature.

The expert UI 115 in the guided mode 165 may also be triggered by receipt of the query dataset 510 at the query module 425 if the query dataset 510 mentions one or more features or feature values that are previously unknown to the machine learning engine 210. In such a case, the guided mode 165 may cause the dataset analysis system 205 to send the query dataset 510 to the expert device 110 and request input from the one or more experts 105 regarding the previously-unknown features and/or feature values. Alternately, the guided mode 165 may identify the previously-unknown features to the expert device 110 and request that the one or more experts 105 provide one or more patient population source seeds with which to generate one or more simulated patient population datasets using the previously-unknown features, or answer questions so that the expert UI 115 in the guided mode 165 may automatically generate one or more patient population source seeds with which to generate one or more simulated patient population datasets using the previously-unknown features, so that the machine learning engine 210 can be trained using these newly generated simulated patient population datasets with the previously-unknown features to learn to understand which outcomes are associated with which feature values of the previously-unknown features.

The query device 520 may include one or more computing devices 1500 as illustrated in FIG. 15 and as discussed with respect to FIG. 15. In some cases, the query device 520 may include a subset of the components of the computing device 1500 illustrated in FIG. 15 and/or as discussed with respect to FIG. 15. While the query device 520 and the and/or the dataset analysis system 205 are illustrated as separate computing devices and/or separate sets of computing devices in FIG. 5, in some cases the query device 520 and the dataset analysis system 205 may be co-located on a single set of one or more computing devices 1500, or may share one or more computing devices 1500 in common. In some cases, the dataset analysis system 205 may be alternately referred to as a dataset analysis module, a dataset analysis device, a patient simulation system, a patient simulation module, or a patient simulation device.

In some cases, the querying users 505 may also receive reputation scores of their own. Reputation scores for the a querying user 505 may impact how much positive or negative feedback 550 from the querying user 505 impacts re-selection of simulated patient datasets for the training dataset 290. For example, feedback 550 from a querying user 505 with a high reputation score (e.g., above a threshold reputation score) may cause the dataset analysis system 205 to modify the number of simulated patient datasets drawn from a certain simulated patient population dataset for the training dataset 290 by more than feedback 550 from a querying user 505 with a low reputation score (e.g., below a threshold reputation score).

FIG. 6 illustrates a sample format for or predicted outcomes.

The outcomes 600 of FIG. 6 provide a format that may be used to predicted outcomes 540.

The outcomes 600 may include likely diagnoses 610 with likelihood probabilities. In the outcomes 600 of FIG. 6, these include a first diagnosis for a first disease 650A with a first likelihood probability 655A, a second diagnosis for a second disease 650B with a second likelihood probability 655B, up to an Nth diagnosis for an Nth disease 650Z with an Nth likelihood probability 655Z.

The outcomes 600 may include recommended tests 615 with recommendation strengths. In the outcomes 600 of FIG. 6, these include a first test 660A with a first recommendation strength 665A, a second test 660B with a second recommendation strength 665B, up to an Nth test 660Z with an Nth recommendation strength 665Z.

The outcomes 600 may include recommended treatments 620 with recommendation strengths. In the outcomes 600 of FIG. 6, these include a first treatment 640A with a first recommendation strength 645A, a second treatment 640B with a second recommendation strength 645B, up to an Nth treatment 640Z with an Nth recommendation strength 645Z.

The outcomes 600 may include identifications of features 625 that factor most into a particular diagnosis (of the diagnoses 610) with levels of importance. In the outcomes 600 of FIG. 6, these include a first feature 670A with a first level of importance 675A, a second feature 670B with a second level of importance 675B, up to an Nth feature 670Z with an Nth level of importance 675Z.

The outcomes 600 may include identifications of features 630 that factor most into a particular test recommendation (of the recommended tests 615) with levels of importance. In the outcomes 600 of FIG. 6, these include a first feature 680A with a first level of importance 685A, a second feature 680B with a second level of importance 685B, up to an Nth feature 680Z with an Nth level of importance 685Z.

The outcomes 600 may include identifications of features 630 that factor most into a particular treatment recommendation (of the recommended treatments 620) with levels of importance. In the outcomes 600 of FIG. 6, these include a first feature 690A with a first level of importance 695A, a second feature 690B with a second level of importance 695B, up to an Nth feature 690Z with an Nth level of importance 695Z.

Figure 7A:
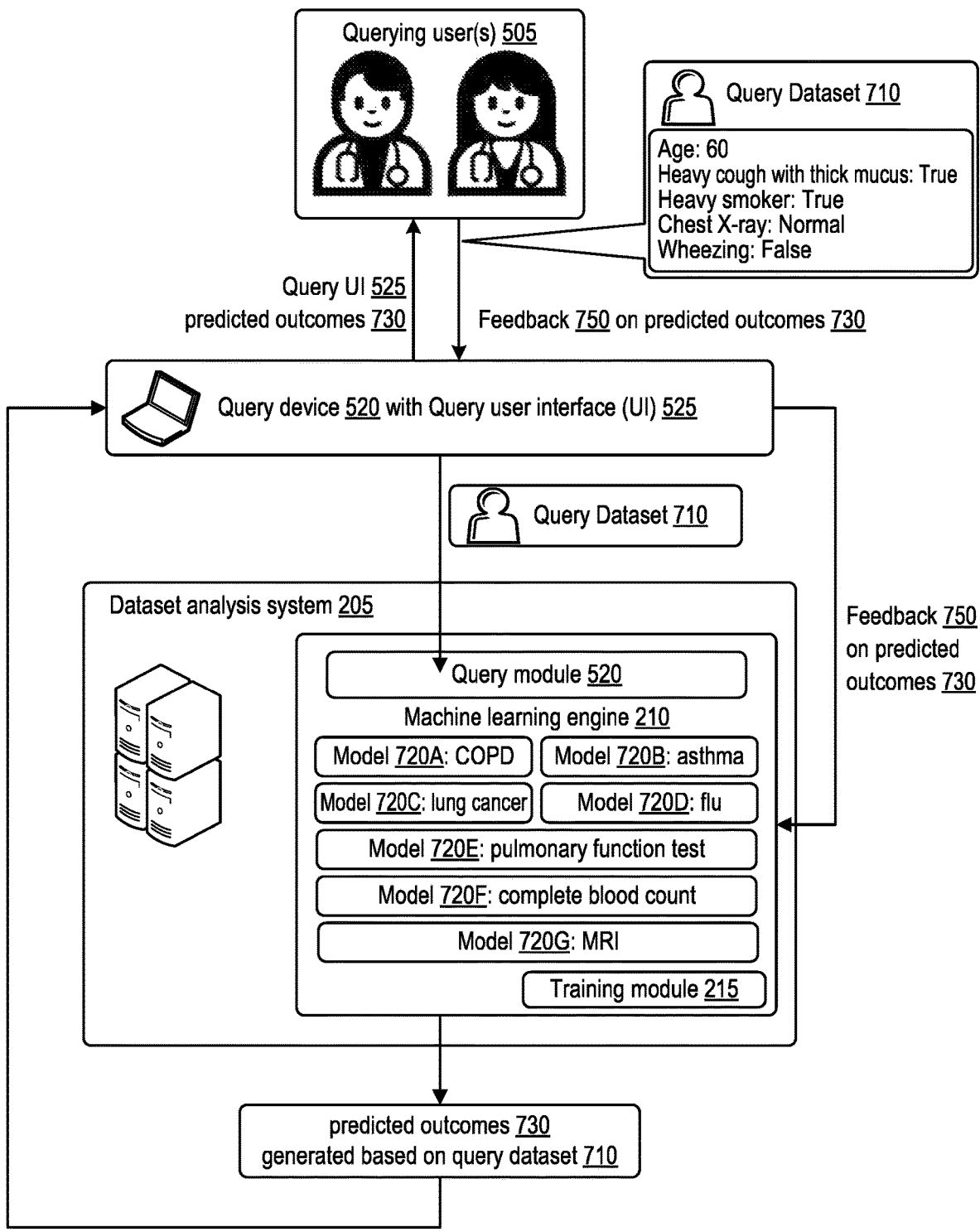
FIG. 7A is a block diagram illustrating generation of predicted outcomes based on an exemplary query.

FIG. 7A is a block diagram illustrating generation of predicted outcomes based on an exemplary query.

In particular, the block diagram 700 of FIG. 7A is a variant of the block diagram 500 of FIG. 5 with examples of various elements. For example, the query dataset 710 of FIG. 7A is an example of the query dataset 510 of FIG. 5. The query dataset 710 identifies five features and five corresponding feature values. The first feature identified in the query dataset 710 is age, for which the corresponding feature value is given as 60. The second feature identified in the query dataset 710 is "heavy cough with thick mucus," for which the corresponding (boolean) feature value is given as true. The third feature identified in the query dataset 710 is "heavy smoker," for which the corresponding (boolean) feature value is given as true. The fourth feature identified in the query dataset 710 is "Chest X-ray," for which the corresponding (category) feature value is given as "Normal." The fifth feature identified in the query dataset 710 is "wheezing," for which the corresponding (boolean) feature value is given as false. As in FIG. 5, the querying users 505 input the query dataset 710 into the query device 520, which sends the query dataset 710 to the query module 520 of the machine learning engine 210 of the dataset analysis system 205.

In this particular non limiting example, the machine learning engine 210 of the dataset analysis system 205 of FIG. 7A includes seven identified AI/ML models, each corresponding to a particular outcome. The models of the machine learning engine 210 of FIG. 7A include a COPD model 720A, an asthma model 720B, a lung cancer model 720C, a flu model 720D, a pulmonary function test model 720E, a complete blood count model 720F, a magnetic resonance imaging (MRI) model 720G. Other models may also exist that are not illustrated in FIG. 7A for the sake of simplicity, as discussed further with respect to FIG. 7B.

The machine learning engine 210 of the dataset analysis system 205 queries each of the models 720A-G with the query dataset 710, and, based on the results of these queries, outputs a set of one or more predicted outcomes 730 generated based on the query dataset 710. An example of the predicted outcomes 730 is illustrated in FIG. 7B. As in FIG. 5, the set of one or more predicted outcomes 730 are sent from the dataset analysis system 205 to the query device 520. Upon receipt of the set of one or more predicted outcomes 730, the query device 520 renders and displays the set of one or more predicted outcomes 730 for the one or more querying users 505 to review. In response, the one or more querying users 505 input feedback 750 on the one or more predicted outcomes 730 into the query device 520. The query device sends the feedback 750 to the dataset analysis system 205, which provides the feedback 750 to the machine learning engine 210, and optionally tunes one or more models of the machine learning engine 210 based on changes to the metadata (expert reputation 350, simulated patient population dataset reputation score 355) as discussed with respect to FIG. 5. The training dataset 290 may be re-generated when metadata is updated. An amount of simulated patient datasets from a simulated patient population dataset that are included in the training dataset may be a function of the expert reputation score 350 and/or simulated patient population reputation 355 and/or of the initial count 218 (how many were generated in the population) and/or of characteristics of the machine learning engine 210. For example, if population has poor reputation, only 5% of simulated patient datasets from that population will find their way into the training dataset. When a training dataset 290 is re-generated. the machine learning engine then does the training all over again using the re-generated training set.

FIG. 7B illustrates exemplary predicted outcomes generated based on the exemplary query of FIG. 7A.

The set of predicted outcomes 730 generated based on the query dataset 710 of FIG. 7B are an example of the outcomes 600 of FIG. 6.

The predicted outcomes 730 may include likely diagnoses 735 with likelihood probabilities. In the predicted outcomes 730 of FIG. 7B, these include a diagnosis for COPD 740A with a likelihood probability 742A of 70%, a diagnosis for lung cancer 740B with a likelihood probability 742B of 65%, a diagnosis for asthma 740C with a likelihood probability 742C of 10%, and a diagnosis for the flue 740D with a likelihood probability 742D of 5%. The diagnosis for COPD 740A and the likelihood probability 742A may be generated using the COPD model 720A. The diagnosis for asthma 740C and the likelihood probability 742C may be generated using the asthma model 720B. The diagnosis for lung cancer 740B and the likelihood probability 742B may be generated using the lung cancer model 720C. The diagnosis for the flu 740D and the likelihood probability 742D may be generated using the flu model 720D.

The predicted outcomes 730 may include recommended tests 745 with recommendation strengths. In the predicted outcomes 730 of FIG. 7B, these include a pulmonary function test 750A with a recommendation strength 752A of 42%, a complete blood count test 750B with a recommendation strength 752B of 10%, and a magnetic resonance imaging (MRI) test 750C with a recommendation strength 752C of 6%. The recommendation for the pulmonary function test 750A and the recommendation strength 752A may be generated using the pulmonary function test model 720E. The recommendation for the complete blood count test 750B and the recommendation strength 752B may be generated using the complete blood count model 720F. The recommendation for the MRI test 750C and the recommendation strength 752C may be generated using the MRI model 720G.

The predicted outcomes 730 may include identifications of features 755 that factor most into the COPD diagnosis 740A with the 70% likelihood probability 742A, along with levels of importance. In the predicted outcomes 730 of FIG. 7B, these include a "heavy cough" feature 760A with an effect on likelihood of diagnosis 762A being an increase of 24%, a "normal chest X-ray" feature 760B with an effect on likelihood of diagnosis 762B being an increase of 21%, and a "history of smoking" feature 760C with an effect on likelihood of diagnosis 762C being a increase of 20%. In some cases, the features 755 may be identified using the COPD model 720A.

These percentage effects may be identified, for example, based on risk percentages in one category subtracted from risk percentages from other categories. For example, if risk of breast cancer in females is 90% and risk of breast cancer in males is 10%, then being female has a +80% effect on likelihood of breast cancer (90%-10%), and being male has a -80% effect on likelihood of breast cancer (10%-90%). For a feature with more possible feature values, such as a "cough" feature whose values may be "light," "medium," and "heavy," then an average of the risks at the feature values whose effects are not being determined are subtracted from the risk at the feature value whose effect is being calculated. For example, if "heavy" cough has a 90% risk of lung cancer, "medium" cough has a 20% risk of lung cancer, and "light" cough has a 10% risk of lung cancer, then the effect on risk of lung cancer of a "heavy" cough is +75% (90%-15%, where 15% is an average of 10% and 20%).

The predicted outcomes 730 may include identifications of features 765 that factor most into the lung cancer diagnosis 740B with the 65% likelihood probability 742B, along with levels of importance. In the predicted outcomes 730 of FIG. 7B, these include a "history of smoking" feature 770A with an effect on likelihood of diagnosis 772A being an increase of 30%, a "heavy cough" feature 770B with an effect on likelihood of diagnosis 772B being an increase of 24%, and a "normal chest X-ray" feature 770C with an effect on likelihood of diagnosis 772C being a decrease of 11%. In some cases, the features 755 may be identified using the lung cancer model 720C.

The predicted outcomes 730 may include identifications of features 775 that factor most into the asthma diagnosis 740C with the10% likelihood probability 742C, along with levels of importance. In the predicted outcomes 730 of FIG.

7B, these include a "lack of wheezing" feature 780A with an effect on likelihood of diagnosis 782A being a decrease of 20%, a "heavy cough with mucus" feature 780B with an effect on likelihood of diagnosis 782B being a decrease of 13%, and a "normal chest X-ray" feature 780C with an effect on likelihood of diagnosis 782C being a decrease of 11%. In some cases, the features 755 may be identified using the lung cancer model 720C.

The predicted outcomes 730 may include follow-on questions 785 for the one or more querying users 505. The follow-on questions 785, if answered, may potentially allow the machine learning engine 210 to provide more accurate predicted outcomes. In the predicted outcomes 730 of FIG. 7B, these follow-on questions 785 include a question 790A asking if there is family history of lung cancer and a question 790B asking if there is the patient is male or female. Both may be answered within the predicted outcomes 730 as illustrated in FIG. 7B, which may be representative of how the predicted outcomes 730 may be displayed through the query UI 525 that also accepts inputs (e.g., to answer the follow-on questions 785) from the querying users 505. Follow-on questions may be generated and presented to the query user 505 by identifying features that have a high effect on one or more outcomes but that are not provided in the query dataset 710. By receiving the follow-on questions, the query user 505 may then know to add such information to the next query dataset if the query user 505 is able to find this information. If two outcomes have likelihood probabilities or recommendation strengths that are within a predetermine range (e.g., 10%) of one another, such as the COPD diagnosis 740A having the 70% likelihood probability 742A and the lung cancer diagnosis 740B having the 65% likelihood probability 742A, then a follow-on question may be generated and presented to the query user 505 to help differentiate those two outcomes more.

The predicted outcomes 730 may include recommended treatments 792 with recommendation strengths. In the predicted outcomes 730 of FIG. 7B, these include a drug treatment 795A with a recommendation strength 798A of 35%, a surgery treatment 795B with a recommendation strength 798B of 12%, and a vitamin treatment 795C with an recommendation strength 798C of 4%.

While the predicted outcomes 730 do not illustrate identifications of features that factor most into each of the flu diagnosis 740D with the 5% likelihood probability 742D (of the diagnoses 735) with levels of importance, it should be understood that this may be included. While the predicted outcomes 730 to not illustrate identifications of features that factor most into each of the test recommendations (of the recommended tests 745) with levels of importance, it should be understood that these may be included. While the predicted outcomes 730 to not illustrate identifications of features that factor most into each of the treatment recommendations (of the recommended treatments 792) with levels of importance, it should be understood that these may be included.

In some cases, the outcomes here may be limited to the top N outcomes based on probability or strength. For example, if another disease diagnosis has only a 1% or 2% likelihood probability, it may be omitted from the list of diagnoses 735. Similarly, if another recommended test has only a 1% or 2% recommendation strength, it may be omitted from the list of recommended tests 745. Similarly, if another recommended treatment has only a 1% or 2% recommendation strength, it may be omitted from the list of recommended treatments 792.

FIG. 8 illustrates an example of an expert user interface for analyzing an information source via an assisted/supervised natural language processing (NLP) operation.

In particular, an example 800 of an expert UI 115 for analyzing an information source 810 via the assisted/supervised NLP mode 170 is illustrated in FIG. 8. A source 815 is given as the National Center for Biotechnology Information, and a hyperlink is provided. The type of source 820 is identified as abstract, a journal, and a publication. The source may be associated with a particular outcome 825, which in this case is a lung cancer diagnosis, which may correspond to an outcome identifier (ID) of "LungCa" in the training dataset 290.

The NLP algorithm identifies four features within the information source such that parsing of the information source ties these four features to the lung cancer diagnosis outcome 825. These four features are identifies as symptoms, namely hemoptysis, dyspnea, cough, and chest pain. Odds ratios for having the outcome 825 based on each of the features are also found by the NLP algorithm, with hemoptysis indicating a 6:39 odds ratio of having the outcome 825, dyspnea indicating a 2:73 odds ratio of having the outcome 825, cough indicating a 2:64 odds ratio of having the outcome 825, and chest pain indicating a 2:20 odds ratio of having the outcome 825. All four features are identified as having (boolean) categorical feature values with possible category values being "yes" and "no."

The NLP algorithm identifies that Hemoptysis and dyspnea are new and do not already appear as features in the training dataset 290, while cough already appears as a feature in the training dataset 290, and chest pain likely appears as a feature in the training dataset 290 (since "chest pains" appears). Checkboxes appear next to each feature to insert or keep the feature in the training dataset 290, allowing one or more experts 105 to assist or supervise. Varius other customizations are also permitted by the NLP algorithm, allowing one or more experts 105 to assist or supervise, for example editing odds ratios, editing possible category values, choosing how each feature will be handled, and creating a new outcome identifier for the outcome 825.

Figure 9:
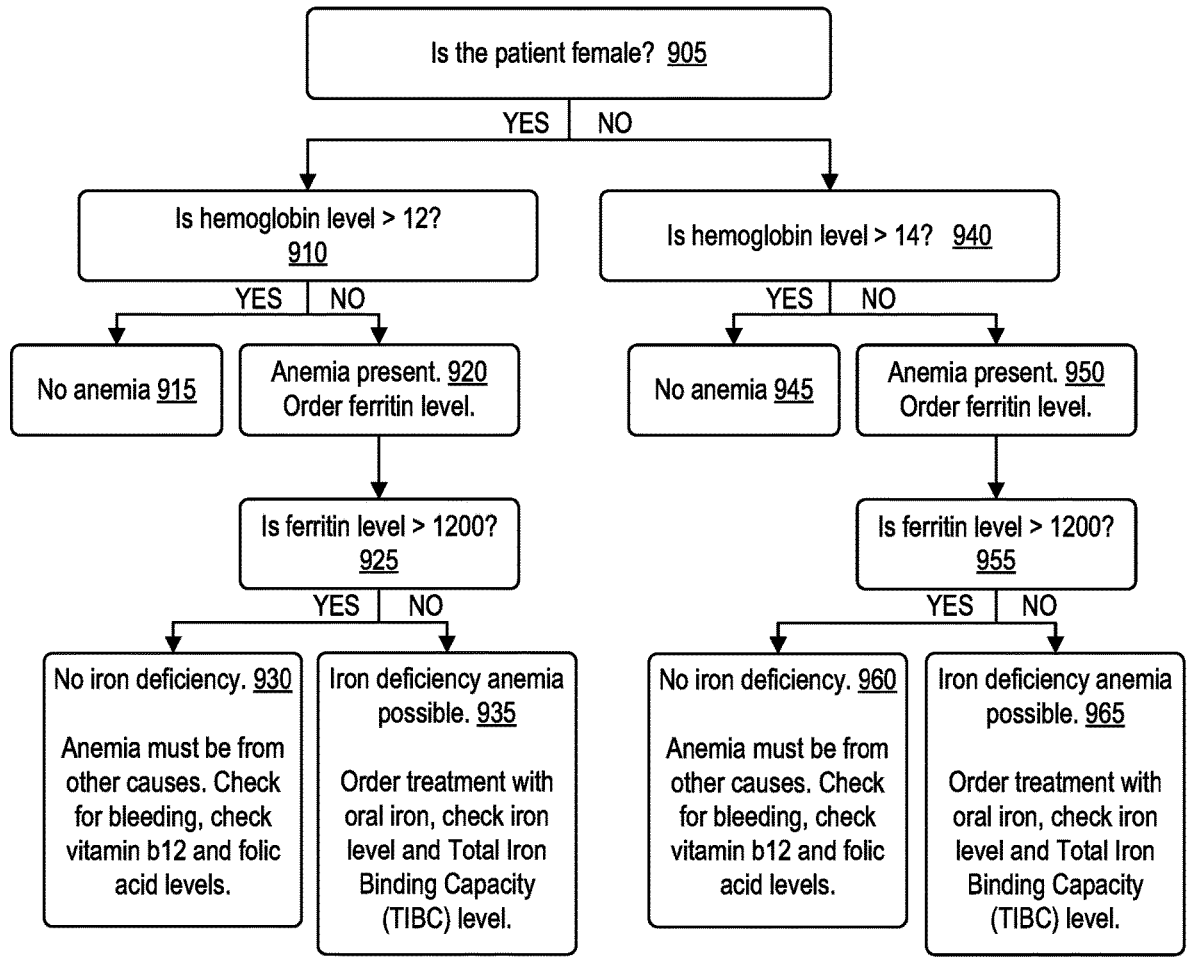
FIG. 9 illustrates an example decision tree that may be used in generating predicted outcomes.

FIG. 9 illustrates an example decision tree that may be used in generating predicted outcomes.

The decision tree 900 concerns a particular outcome—specifically, an anemia diagnosis. The decision tree 900 may be automatically generated by the machine learning engine 210 as at least part of an AI/ML model concerning the outcome of an anemia diagnosis, and may be generated based on training of the machine learning engine 210 using one or more simulated patient population datasets. The decision tree 900 may be generated, for example, using a random forests algorithm, or any other AI or ML algorithm otherwise discussed with respect to the machine learning engine 210. It should be understood that the decision tree 900 may be a simplified variant of a decision tree or other AI/ML model concerning the outcome of an anemia diagnosis. For example, percentages of likelihood are left out of the decision tree 900 for simplicity, but may be present at each node in the tree.

The decision tree 900 begins with a first decision 905—is the patient female? If features of the query dataset 510 being analyzed using the decision tree 900 indicate that the patient is female, then a next decision 910 is reached, asking—is hemoglobin level greater than 12? If features of the query dataset 510 being analyzed using the decision tree 900 indicate that the hemoglobin level is greater than 12, then a predicted outcome of no anemia 915 is output.

If, at the decision 910, the features of the query dataset 510 being analyzed using the decision tree 900 indicate that the hemoglobin level is less than 12, then an outcome 920 is output requesting that the querying user(s) 505 order a ferritin level test. A next decision 925 is reached once the ferritin level test is ordered, asking—is ferritin level greater than 1200? If features of the query dataset 510 being analyzed using the decision tree 900 indicate that the ferritin level is greater than 1200, then a predicted outcome of no iron deficiency 930 is output, indicating that anemia must be from other causes, such as bleeding, vitamin 12 levels, and folic acid levels.

If, at the decision 925, the features of the query dataset 510 being analyzed using the decision tree 900 indicate that the ferritin level is less than 1200, then then a predicted outcome of possible iron deficiency anemia 935 is output, indicating that anemia may be due to iron deficiency, and recommending oral iron treatments and tests of iron level and total iron binding capacity (TIBC) level.

If, at the decision 905, the features of the query dataset 510 being analyzed using the decision tree 900 indicate that the patient is not female, then then a next decision 940 is reached, asking—is hemoglobin level greater than 14? If features of the query dataset 510 being analyzed using the decision tree 900 indicate that the hemoglobin level is greater than 14, then a predicted outcome of no anemia 945 is output.

If, at the decision 940, the features of the query dataset 510 being analyzed using the decision tree 900 indicate that the hemoglobin level is less than 14, then an outcome 950 is output requesting that the querying user(s) 505 order a ferritin level test. A next decision 955 is reached once the ferritin level test is ordered, asking—is ferritin level greater than 1200? If features of the query dataset 510 being analyzed using the decision tree 900 indicate that the ferritin level is greater than 1200, then a predicted outcome of no iron deficiency 960 is output, indicating that anemia must be from other causes, such as bleeding, vitamin 12 levels, and folic acid levels.

If, at the decision 955, the features of the query dataset 510 being analyzed using the decision tree 900 indicate that the ferritin level is less than 1200, then then a predicted outcome of possible iron deficiency anemia 965 is output, indicating that anemia may be due to iron deficiency, and recommending oral iron treatments and tests of iron level and total iron binding capacity (TIBC) level.

In some cases, the decision tree 900 may be input manually by one or more experts 105 rather than generated as at least part of a model by the machine learning engine 210. In some cases, the decision tree 900 may be edited by the one or more experts 105 via the expert UI 115 of the expert device 910.

FIG. 10 illustrates an example expert user interface for generating a patient population source seed.

The example 1000 expert user interface 115 for generating the patient population source seed 120 of FIG. 10 includes controls through which an expert 105 may select feature parameters 1002 for simulated patients (simulated patient datasets) in a simulated patient population dataset 1005. A gender feature parameter 1010 includes boxes checked for "male" and "female" but not "other" or "N/A," indicating that the simulated patient population 1005 will be generated so that each simulated patient dataset is selected at random with either a "male" or "female" gender feature value, but not an "other" or a "N/A" feature value. In some cases, additional controls in the expert user interface 115 may be present to select a ratio (e.g., 50% male and 50% female). An age feature parameter 1015 identifies an acceptable range of feature values between 47 and 91, indicating that the simulated patient population 1005 will be generated so that ages for its simulated patient datasets are each selected at random, optionally according to a probability distribution as in FIG. 13, within the acceptable range between 47 and 91.

A body temperature (° F.) feature parameter 1020 identifies an acceptable range of feature values between 96 and 100, indicating that the simulated patient population 1005 will be generated so that body temperatures for its simulated patient datasets are each selected at random, optionally according to a probability distribution as in FIG. 13, within the acceptable range between 96 and 100. A body mass index (BMI) feature parameter 1025 identifies an acceptable range of feature values between 27 and 45, indicating that the simulated patient population 1005 will be generated so that BMI values for its simulated patient datasets are each selected at random, optionally according to a probability distribution as in FIG. 13, within the acceptable range between 27 and 45. A pulse rate (beats per minute (bpm)) feature parameter 1030 identifies an acceptable range of feature values between 60 and 95, indicating that the simulated patient population 1005 will be generated so that pulse rate (bpm) values for its simulated patient datasets are each selected at random, optionally according to a probability distribution as in FIG. 13, within the acceptable range between 60 and 95.

A systolic blood pressure feature parameter 1035 identifies an acceptable range of feature values between 100 and 139, indicating that the simulated patient population 1005 will be generated so that systolic blood pressure values for its simulated patient datasets are each selected at random, optionally according to a probability distribution as in FIG. 13, within the acceptable range between 100 and 139. A distolic blood pressure feature parameter 1040 identifies an acceptable range of feature values between 50 and 84, indicating that the simulated patient population 1005 will be generated so that distolic blood pressure values for its simulated patient datasets are each selected at random, optionally according to a probability distribution as in FIG. 13, within the acceptable range between 50 and 84.

A respiratory rate feature parameter 1045 identifies an acceptable range of feature values between 12 and 18, indicating that the simulated patient population 1005 will be generated so that respiratory rate values for its simulated patient datasets are each selected at random, optionally according to a probability distribution as in FIG. 13, within the acceptable range between 12 and 18. An arterial $O_2$ saturation (Sa02%) feature parameter 1050 identifies an acceptable range of feature values between 94 and 100, indicating that the simulated patient population 1005 will be generated so that arterial $O_2$ saturation (Sa02%) values for its simulated patient datasets are each selected at random, optionally according to a probability distribution as in FIG. 13, within the acceptable range between 94 and 100. A supplied air $O_2$% (FiO2%) feature parameter 1055 identifies an acceptable range of feature values between 21 and 27, indicating that the simulated patient population 1005 will be generated so that supplied air $O_2$ % (FiO2%) values for its simulated patient datasets are each selected at random, optionally according to a probability distribution as in FIG. 13, within the acceptable range between 21 and 27.

When acceptable ranges of feature values are given in a feature parameter, such as in the feature parameters 1015, 1020, 10125, 1030, 1035, 1040, 1045, 1050, and 1055, the bounds of the range may be optionally included in the acceptable range of feature values or excluded from the acceptable range of feature values. Similarly, if a minimum threshold feature value or a maximum threshold feature value is given in a feature parameter, the threshold feature value may be optionally included in the resulting acceptable range of feature values or excluded from the resulting acceptable range of feature values. In some cases, additional controls in the expert user interface 115 may be present to select a distribution of ages within the acceptable ranges of feature values, such as a Gaussian distribution or any other type of distribution discussed herein.

The example 1000 expert user interface 115 for generating the patient population source seed 120 of FIG. 10 also includes outcomes 1060 corresponding to the feature parameters 1002. The outcomes 1060 identified include acute diagnoses 1065, which here include pneumonia and pulmunary embolus. Both pneumonia and pulmunary embolus include a label "pulmunary" indicating that these are pulmonary diseases—this label may optionally be present in the simulated patient datasets that will be generated based on the patient population source seed 120. Other diseases may include other labels for other categories of diseases, such as "cardiovascular," "musculoskeletal," "gastrointestinal," and so forth. The expert 105 may add such a label manually, or the label may be added automatically based on previously known information about these diagnoses. Pulmunary embolus also includes a "can't miss!" label indicating that this diagnosis could be particularly dangerous and should not be overlooked. Again, the expert 105 may add such a label manually, or the label may be added automatically based on previously known information about these diagnoses. In some cases, an outcome with the "can't miss!" label may not be removable from predicted outcomes, even if probabilities are low.

The outcomes 1060 identified include recommended tests 1070, which here include a chest computed tomography (CT) scan with intravenous (IV) dye. The outcomes 1060 identified include chronic diseases 1075, which here include chronic nontuberculous mycobacteria lung infection, which again here is labeled "pulmunary" based on disease type, either due to input from an expert 105 or previously known information about this diagnosis. A pull-down menu identifies other chronic diagnoses 1075 that may be selected by the expert 105 via the expert UI 115, such as chronic COPD, chronic asthma, Churg-Strauss syndrome, chronic left ventricle heart failure (LVHF), hypertrophic cardiomyopathy, dilated cardiomyopathy, and chronic tricuspid regurgitation (TR).

The example 1000 expert user interface 115 for generating the patient population source seed 120 of FIG. 10 also includes a count 1080 of 5,000, indicating that 5,000 simulated patient datasets will be generated based on the feature parameters 1002 and the outcomes 1060 corresponding to the feature parameters 1002.

Figure 11:
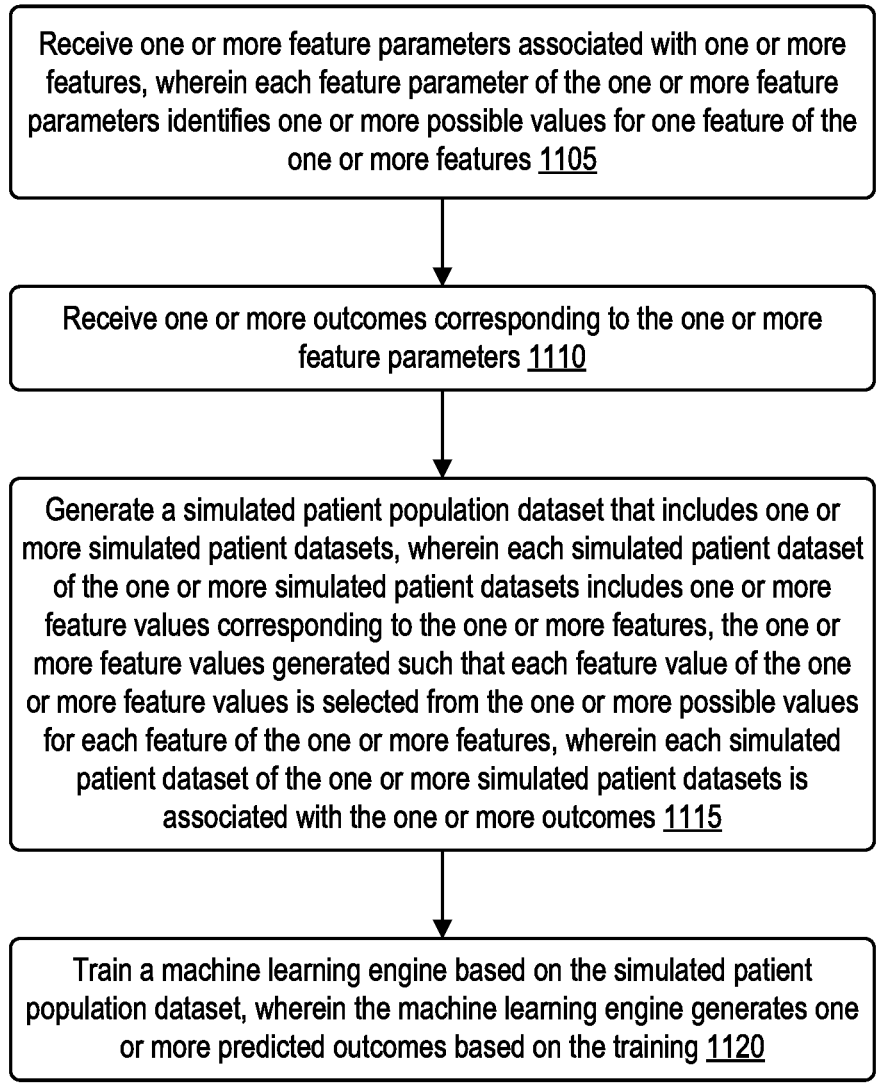
FIG. 11 is a flow diagram illustrating a method of generating and processing simulated patient information.

FIG. 11 is a flow diagram illustrating a method of generating and processing simulated patient information.

Step 1105 includes receiving one or more feature parameters associated with one or more features, wherein each feature parameter of the one or more feature parameters identifies one or more possible values for one feature of the one or more features.

Step 1110 includes receiving one or more outcomes corresponding to the one or more feature parameters.

Step 1115 includes generating a simulated patient population dataset that includes one or more simulated patient datasets, wherein each simulated patient dataset of the one or more simulated patient datasets includes one or more feature values corresponding to the one or more features, the one or more feature values generated such that each feature value of the one or more feature values is selected from the one or more possible values for each feature of the one or more features, wherein each simulated patient dataset of the one or more simulated patient datasets is associated with the one or more outcomes.

Step 1120 training a machine learning engine based on the simulated patient population dataset, wherein the machine learning engine generates one or more predicted outcomes based on the training.

FIG. 12A illustrates a first exemplary simulated patient population dataset.

The simulated patient population dataset 1200 of FIG. 12A is illustrated as a table and includes 30 simulated patient datasets. Each of the 30 simulated patient datasets is represented in the simulated patient population dataset 1200 as one of the rows underneath the top row of the table, which identifies column legends. Each column of the table identifies either a feature or an outcome. For a column corresponding to a feature, each cell in that column that is in one of the simulated patient datasets includes a feature value associated with that feature. For a column corresponding to an outcome, each cell in that column that is in one of the simulated patient datasets includes an outcome value associated with that outcome.

The features identified in the simulated patient population dataset 1200 include age ("Age"), smoking history in pack years ("SmokerHx"), cough ("Cough"), hemoptysis ("Hemoptysis"), and state of health ("Health"). The outcomes identified in the simulated patient population dataset 1200 include a lung cancer diagnosis ("LungCa"), chronic benign cough ("BeningChronicCough"), a recommendation for a chest X-ray posteroanterior (PA)+lateral ("ChestXRayP-ALat"), and a recommendation for a portable chest X-ray posteroanterior (PA) ("PortableCxray"). The simulated patient datasets are illustrated with numeric feature values for all features and numeric outcome values for all outcomes. However, the outcome values in the simulated patient population dataset 1200 are all actually Boolean values, as they are all either 0 (false) or 1 (true). Certain features in the simulated patient population dataset 1200 also appear to have Boolean feature values (0=false or 1=true), such as state of health. Other features in the simulated patient population dataset 1200 use numeric feature values, such as age and smoking history in pack years. Other features in the simulated patient population dataset 1200 use numeric feature values as stand-in values for categories or severity measurements, such as the cough and hemoptysis features, which include many "2" and "3" feature values. In the context of the cough and hemoptysis features the number 1 represents "not available," the number 2 represents "no," and the number 3 represents "yes." Alternately, the numbers may represent different degrees of severity of coughing and hemoptysis, respectively, along a range of severity values.

FIG. 12B illustrates a second exemplary simulated patient population dataset.

Like the simulated patient population dataset 1200 of FIG. 12A, the simulated patient population dataset 1250 of FIG. 12B is illustrated as a table and includes 30 simulated patient datasets. The columns of the simulated patient population dataset 1250 of FIG. 12B identify the same features and outcomes as the columns of the simulated patient population dataset 1200 of FIG. 12A, and in the same order.

One difference between the simulated patient population dataset 1250 of FIG. 12B and the simulated patient population dataset 1200 of FIG. 12A is that the simulated patient population dataset 1250 of FIG. 12B includes some feature values that are marked as not available ("NA"). In the simulated patient population dataset 1200 of FIG. 12A, the same cells were filled in with feature values, which may have been default feature values for those features. For example, the cells in the "Age" column in the simulated patient population dataset 1250 of FIG. 12B in which data is marked as not available are all filled in with the age "35" in simulated patient population dataset 1200 of FIG. 12A. Thus, 35 may have been set as a default age when generating the simulated patient population dataset 1200 of FIG. 12A. Similarly, cells in the "SmokrHx" column in the simulated patient population dataset 1250 of FIG. 12B in which data is marked as not available are all filled in with the value "0" in simulated patient population dataset 1200 of FIG. 12A, which may have been set as the default value for the "SmokrHx" feature when generating the simulated patient population dataset 1200 of FIG. 12A. Cells in the "Cough" column in the simulated patient population dataset 1250 of FIG. 12B in which data is marked as not available are all filled in with the value 2 ("no") in simulated patient population dataset 1200 of FIG. 12A, which may have been set as the default value for the "Cough" feature when generating the simulated patient population dataset 1200 of FIG. 12A. Cells in the "Hemoptysis" column in the simulated patient population dataset 1250 of FIG. 12B in which data is marked as not available are all filled in with the value 2 ("no") in simulated patient population dataset 1200 of FIG. 12A, which may have been set as the default value for the "Hemoptysis" feature when generating the simulated patient population dataset 1200 of FIG. 12A.

FIG. 13A illustrates an exemplary distribution of feature values for a particular feature within a simulated patient population dataset according to a feature parameter designating a symmetric Gaussian distribution.

As discussed with respect to FIG. 1, feature parameters 122 may identify distributions. The example distribution 1300 shown in FIG. 13A represents one or more simulated patient population datasets generated using feature parameters 122 that identify a Gaussian distribution for a "patient body mass index (BMI)" feature, with the mean of the BMI feature value being 22 kg/m² and the standard deviation of the BMI feature value being 3.5 kg/m². The horizontal X axis in the distribution 1300 indicates feature value 1310—that is, BMI value. The vertical Y axis in the distribution 1300 indicates a frequency of each feature value in the one or more simulated patient population datasets generated based on the feature parameters 122.

FIG. 14A illustrates an exemplary outcome and feature relationship interface relating a positive lung cancer diagnosis outcome to various feature parameters, including a focus on a cough feature.

The outcome and feature relationship interface 1400 of FIG. 14A may represent another non limiting example of at least one part of the expert UI 115. The outcome and feature relationship interface 1400 identifies information about a particular outcome 1405—specifically, a lung cancer diagnosis in FIG. 14A. The outcome and feature relationship interface 1400 may be part of the expert UI 115.

The outcome and feature relationship interface 1400 identifies the outcome 1405 as well as relevant features 1410 for which feature parameters are included in a particular patient population source seed 120. The patient population source seed 120 here includes four relevant features 1410 that are identified in FIG. 14A, namely age, SmokerHx, hemoptysis, and cough. Of those four relevant features 1410, age is identified by its feature parameters as ranging from 0 to 130 and having a Gaussian distribution with a mean of 130 and a standard deviation of 30, as represented by the indicator "gaussian I 300, 100, 0, 300." SmokerHx is identified by its feature parameters as ranging from 0 to 300 and having a Gaussian distribution with a mean of 300 and a standard deviation of 100, as represented by the indicator "gaussian I 130, 30, 0, and 130." Hemoptysis is identified by its feature parameters as having a category distribution in which the feature value 1 (data unavailable) corresponds to a 0 percent frequency/probability of the outcome 1405, the feature value 2 (no) corresponds to a 20 percent frequency/probability of the outcome 1405, and the feature value 3 (yes) corresponds to an 80 percent frequency/probability of the outcome 1405. Cough is identified by its feature parameters as having a category distribution in which the feature value 1 (data unavailable) corresponds to a 0 percent frequency/probability of the outcome 1405, the feature value 2 (no) corresponds to a 40 percent frequency/probability of the outcome 1405, and the feature value 3 (yes) corresponds to an 60 percent frequency/probability of the outcome 1405.

The outcome and feature relationship interface 1400 identifies a highlighted feature 1415 of the relevant features 1410 as being the cough feature, and identifies possible feature values 1420 for the cough feature being 1 (data unavailable), 2 (no cough present), 3 (yes, cough present). A count 1425 is identified of 10 patients to be generated in the simulated patient population dataset based on this patient population seed. A distribution 1445 graphs the 10 patients from the count along a plane. The horizontal X axis of the distribution 1445 represents feature values 1430 for the highlighted feature 1415 (cough) shown ranging from 1 to 4. The vertical Y axis of the distribution 1445 represents expected frequency 1435 of distribution of categories for cough feature in the entire simulated patient population dataset.

FIG. 14B illustrates an exemplary outcome and feature relationship interface relating a positive lung cancer diagnosis outcome to various feature parameters, including a focus on an age feature.

The outcome and feature relationship interface 1450 of FIG. 14B includes much of the same information as was shown in the outcome and feature relationship interface 1440 FIG. 14A, including the lung cancer diagnosis outcome 1405 and the list of four relevant features 1410. In the AI/ML model interface 1450, age is the highlighted feature 1460. A count 1465 of 100 patients is used, and a distribution 1485 is illustrated.

The horizontal X axis of the distribution 1485 of FIG. 13 represents feature values 1470 for the highlighted feature 1460 (age), which ranges from 0 to 130. The vertical Y axis of the distribution 1485 represents the expected frequency 1475 of distribution of values for the age feature in the entire simulated patient population dataset. The resulting distribution 1485 is a skewed asymmetric Gaussian distribution generally showing an increased frequency of positive lung cancer diagnoses at higher ages.

In some cases, some of the data discussed herein, including the various simulated patient datasets, the training dataset 290, and the various models, may be provided to other systems of one or more computing devices 1500, such as an educational system, a law system, an insurance system, and a patient system. These systems may themselves implement any of the devices discussed herein, such as the expert device 110, the dataset generation system 135, the dataset analysis system 205, the query device 520, another computing device 1500 or some combination thereof.

The educational system may be used for educational purposes. The education system can, for example, create a set of questions (true or false, multiple-choice or open-ended). For example, the educational embodiment can use of available simulated patient dataset and generate true or false, or multiple-choice question, as to whether features are relevant to diagnosing, diagnostic test or treatment. Or the educational embodiment may ask "what is the best diagnosis" for a set of displayed features with respective values for the features.

The reputation scores of persons answering questions presented by the educational embodiment (e.g., in a role of experts 105 or querying users 505 or a similar role) can also be stored and treated as feedback, similarly to as is feedback 550 from querying users 505, also to adjust reputation scores 355 for given simulated patient population datasets or reputation scores 350 for experts 105. Scores may be shared with to users, groups or users, or used to be compared against scores of other users, groups of users. Groups of user may include medical students, licensed nurses, physicians, and the like and/or users in specific geographical locations. Contests can be organized for groups of persons to compete against one another for high reputation scores.

The educational system can also provide access to medical sources, references, data sources, names of experts, journal articles, medical textbooks, and the like associated with given outcomes or features.

Prizes, including, monetary prizes can be offered by the educational embodiment to motivate persons to answer questions or otherwise interact, and especially to provide feedback.

The law system is intended to be used by legal professionals (lawyers, legal specialists, malpractice specialists, patients or patients' families, and the like) to enable identification or avoidance of medical malpractice, and in particular misdiagnosis, as a cause of injury or death of a patient.

Medical records and related documentation can provide querying data to be provided by operator of such law system to see if the recommended diagnostic or treatment path has been followed. If not, adjustments to therapy may be suggested, and if this happens, after unwanted outcome such law embodiment can help identify possible medical malpractice or below standard care.

The insurance system is intended to provide access to the methods here in included, to insurance-related persons, such as case managers, insurance or claim specialists, physicians, hospital administration personnel, clinic personnel, and insurance agents and insurance companies Like the law system, the Insurance embodiment enables doctors, to follow the most recommended, and most cost-effective, or otherwise optimized, diagnostic path. Such path can save resources, or only use these covered within patients insurance policy.

The patient system is intended to provide access to the medical diagnosis system to medical patients, so that patients understand the basis for a diagnosis and if necessary, to alert the patient to diagnoses associated with high mortality or acuity and the level of follow up care or help associated with such diagnoses. The patient system can also allow patients to schedule appointments, receive and transmit encrypted medical records and medical information, and streamline history taking prior to an appointment. The patient system can also retrieve and present information about third party support groups or social networks related to a patient's diagnosis or medical condition, and generate documentation for the examining physician related to a diagnosis or medical condition based on patients provided values of features.

In some cases, patient embodiment may also store and retrieve information related to that one patient, including medical history, examination and lab results, etc.

FIG. 15 illustrates an exemplary computing system 1500 that may be used to implement some aspects of the technology. For example, any of the computing devices, computing systems, network devices, network systems, servers, and/or arrangements of circuitry described herein may include at least one computing system 1500, or may include at least one component of the computer system 1500 identified in FIG. 15. The computing system 1500 of FIG. 15 includes one or more processors 1510 and memory units 1520. Each of the processor(s) 1510 may refer to one or more processors, controllers, microcontrollers, central processing units (CPUs), graphics processing units (GPUs), arithmetic logic units (ALUs), accelerated processing units (APUs), digital signal processors (DSPs), application specific integrated circuits (ASICs), field-programmable gate arrays (FPGAs), or combinations thereof. Each of the processor(s) 1510 may include one or more cores, either integrated onto a single chip or spread across multiple chips connected or coupled together. Memory 1520 stores, in part, instructions and data for execution by processor 1510. Memory 1520 can store the executable code when in operation. The system 1500 of FIG. 15 further includes a mass storage device 1530, portable storage medium drive(s) 1540, output devices 1550, user input devices 1560, a graphics display 1570, and peripheral devices 1580.

The components shown in FIG. 15 are depicted as being connected via a single bus 1590. However, the components may be connected through one or more data transport means. For example, processor unit 1510 and memory 1520 may be connected via a local microprocessor bus, and the mass storage device 1530, peripheral device(s) 1580, portable storage device 1540, and display system 1570 may be connected via one or more input/output (I/O) buses.

Mass storage device 1530, which may be implemented with a magnetic disk drive or an optical disk drive, is a non-volatile storage device for storing data and instructions for use by processor unit 1510. Mass storage device 1530 can store the system software for implementing some aspects of the subject technology for purposes of loading that software into memory 1520.

Portable storage device 1540 operates in conjunction with a portable non-volatile storage medium, such as a floppy disk, compact disk or Digital video disc, to input and output data and code to and from the computer system 1500 of FIG. 15. The system software for implementing aspects of the subject technology may be stored on such a portable medium and input to the computer system 1500 via the portable storage device 1540.

The memory 1520, mass storage device 1530, or portable storage 1540 may in some cases store sensitive information, such as transaction information, health information, or cryptographic keys, and may in some cases encrypt or decrypt such information with the aid of the processor 1510. The memory 1520, mass storage device 1530, or portable storage 1540 may in some cases store, at least in part, instructions, executable code, or other data for execution or processing by the processor 1510.

Output devices 1550 may include, for example, communication circuitry for outputting data through wired or wireless means, display circuitry for displaying data via a display screen, audio circuitry for outputting audio via headphones or a speaker, printer circuitry for printing data via a printer, or some combination thereof. The display screen may be any type of display discussed with respect to the display system 1570. The printer may be inkjet, laserjet, thermal, or some combination thereof. In some cases, the output device circuitry 1550 may allow for transmission of data over an audio jack/plug, a microphone jack/plug, a universal serial bus (USB) port/plug, an Apple® Lightning® port/plug, an Ethernet port/plug, a fiber optic port/plug, a proprietary wired port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. Output devices 1550 may include any ports, plugs, antennae, wired or wireless transmitters, wired or wireless transceivers, or any other components necessary for or usable to implement the communication types listed above, such as cellular Subscriber Identity Module (SIM) cards.

Input devices 1560 may include circuitry providing a portion of a user interface. Input devices 1560 may include an alpha-numeric keypad, such as a keyboard, for inputting alpha-numeric and other information, or a pointing device, such as a mouse, a trackball, stylus, or cursor direction keys. Input devices 1560 may include touch-sensitive surfaces as well, either integrated with a display as in a touchscreen, or separate from a display as in a trackpad. Touch-sensitive surfaces may in some cases detect localized variable pressure or force detection. In some cases, the input device circuitry may allow for receipt of data over an audio jack, a microphone jack, a universal serial bus (USB) port/plug, an Apple® Lightning® port/plug, an Ethernet port/plug, a fiber optic port/plug, a proprietary wired port/plug, a wired local area network (LAN) port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, personal area network (PAN) signal transfer, wide area network (WAN) signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. Input devices 1560 may include any ports, plugs, antennae, wired or wireless receivers, wired or wireless transceivers, or any other components necessary for or usable to implement the communication types listed above, such as cellular SIM cards.

Input devices 1560 may include receivers or transceivers used for positioning of the computing system 1500 as well. These may include any of the wired or wireless signal receivers or transceivers. For example, a location of the computing system 1500 can be determined based on signal strength of signals as received at the computing system 1500 from three cellular network towers, a process known as cellular triangulation. Fewer than three cellular network towers can also be used—even one can be used—though the location determined from such data will be less precise (e.g., somewhere within a particular circle for one tower, somewhere along a line or within a relatively small area for two towers) than via triangulation. More than three cellular network towers can also be used, further enhancing the location's accuracy. Similar positioning operations can be performed using proximity beacons, which might use short-range wireless signals such as BLUETOOTH® wireless signals, BLUETOOTH® low energy (BLE) wireless signals, IBEACON® wireless signals, personal area network (PAN) signals, microwave signals, radio wave signals, or other signals discussed above. Similar positioning operations can be performed using wired local area networks (LAN) or wireless local area networks (WLAN) where locations are known of one or more network devices in communication with the computing system 1500 such as a router, modem, switch, hub, bridge, gateway, or repeater. These may also include Global Navigation Satellite System (GNSS) receivers or transceivers that are used to determine a location of the computing system 1500 based on receipt of one or more signals from one or more satellites associated with one or more GNSS systems. GNSS systems include, but are not limited to, the US-based Global Positioning System (GPS), the Russia-based Global Navigation Satellite System (GLONASS), the China-based BeiDou Navigation Satellite System (BDS), and the Europe-based Galileo GNSS. Input devices 1560 may include receivers or transceivers corresponding to one or more of these GNSS systems.

Display system 1570 may include a liquid crystal display (LCD), a plasma display, an organic light-emitting diode (OLED) display, a low-temperature poly-silicon (LTPO) display, an electronic ink or "e-paper" display, a projector-based display, a holographic display, or another suitable display device. Display system 1570 receives textual and graphical information, and processes the information for output to the display device. The display system 1570 may include multiple-touch touchscreen input capabilities, such as capacitive touch detection, resistive touch detection, surface acoustic wave touch detection, or infrared touch detection. Such touchscreen input capabilities may or may not allow for variable pressure or force detection.

Peripherals 1580 may include any type of computer support device to add additional functionality to the computer system. For example, peripheral device(s) 1580 may include one or more additional output devices of any of the types discussed with respect to output device 1550, one or more additional input devices of any of the types discussed with respect to input device 1560, one or more additional display systems of any of the types discussed with respect to display system 1570, one or more memories or mass storage devices or portable storage devices of any of the types discussed with respect to memory 1520 or mass storage 1530 or portable storage 1540, a modem, a router, an antenna, a wired or wireless transceiver, a printer, a bar code scanner, a quick-response ("QR") code scanner, a magnetic stripe card reader, a integrated circuit chip (ICC) card reader such as a smartcard reader or a EUROPAY®-MASTER-CARD®-VISA® (EMV) chip card reader, a near field communication (NFC) reader, a document/image scanner, a visible light camera, a thermal/infrared camera, an ultraviolet-sensitive camera, a night vision camera, a light sensor, a phototransistor, a photoresistor, a thermometer, a thermistor, a battery, a power source, a proximity sensor, a laser rangefinder, a sonar transceiver, a radar transceiver, a lidar transceiver, a network device, a motor, an actuator, a pump, a conveyer belt, a robotic arm, a rotor, a drill, a chemical assay device, or some combination thereof.

The components contained in the computer system 1500 of FIG. 15 can include those typically found in computer systems that may be suitable for use with some aspects of the subject technology and represent a broad category of such computer components that are well known in the art. That said, the computer system 1500 of FIG. 15 can be customized and specialized for the purposes discussed herein and to carry out the various operations discussed herein, with specialized hardware components, specialized arrangements of hardware components, and/or specialized software. Thus, the computer system 1500 of FIG. 15 can be a personal computer, a hand held computing device, a telephone ("smartphone" or otherwise), a mobile computing device, a workstation, a server (on a server rack or otherwise), a minicomputer, a mainframe computer, a tablet computing device, a wearable device (such as a watch, a ring, a pair of glasses, or another type of jewelry or clothing or accessory), a video game console (portable or otherwise), an e-book reader, a media player device (portable or otherwise), a vehicle-based computer, another type of computing device, or some combination thereof. The computer system 1500 may in some cases be a virtual computer system executed by another computer system. The computer can also include different bus configurations, networked platforms, multi-processor platforms, etc. Various operating systems can be used including Unix®, Linux®, FreeBSD®, FreeNAS®, pfSense®, Windows®, Apple® Macintosh OS® ("MacOS®"), Palm OS®, Google® Android®, Google® Chrome OS®, Chromium® OS®, OPENSTEP®, XNU®, Darwin®, Apple® iOS®, Apple® tvOS®, Apple® watchOS®, Apple® audioOS®, Amazon® Fire OS®, Amazon® Kindle OS®, variants of any of these, other suitable operating systems, or combinations thereof. The computer system 1500 may also use a Basic Input/Output System (BIOS) or Unified Extensible Firmware Interface (UEFI) as a layer upon which the operating system(s) are run.

In some cases, the computer system 1500 may be part of a multi-computer system that uses multiple computer systems 1500, each for one or more specific tasks or purposes. For example, the multi-computer system may include multiple computer systems 1500 communicatively coupled together via at least one of a personal area network (PAN), a local area network (LAN), a wireless local area network (WLAN), a municipal area network (MAN), a wide area network (WAN), or some combination thereof. The multi-computer system may further include multiple computer systems 1500 from different networks communicatively coupled together via the internet (also known as a "distributed" system).

Some aspects of the subject technology may be implemented in an application that may be operable using a variety of devices. Non-transitory computer-readable storage media refer to any medium or media that participate in providing instructions to a central processing unit (CPU) for execution and that may be used in the memory 1520, the mass storage 1530, the portable storage 1540, or some combination thereof. Such media can take many forms, including, but not limited to, non-volatile and volatile media such as optical or magnetic disks and dynamic memory, respectively. Some forms of non-transitory computer-readable media include, for example, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, random access memory (RAM), static RAM (SRAM), dynamic RAM (DRAM), read-only memory (ROM), programmable read-only memory (PROM), erasable programmable read-only memory (EPROM), electrically erasable programmable read-only memory (EEPROM), flash EPROM (FLASHEPROM), cache memory (L1/L2/L3/L4/L5/L15), resistive random-access memory (RRAM/ReRAM), phase change memory (PCM), spin transfer torque RAM (STT-RAM), another memory chip or cartridge, or a combination thereof.

Various forms of transmission media may be involved in carrying one or more sequences of one or more instructions to a processor 1510 for execution. A bus 1590 carries the data to system RAM or another memory 1520, from which a processor 1510 retrieves and executes the instructions. The instructions received by system RAM or another memory 1520 can optionally be stored on a fixed disk (mass storage device 1530/portable storage 1540) either before or after execution by processor 1510. Various forms of storage may likewise be implemented as well as the necessary network interfaces and network topologies to implement the same.

While various flow diagrams provided and described above may show a particular order of operations performed by some embodiments of the subject technology, it should be understood that such order is exemplary. Alternative embodiments may perform the operations in a different order, combine certain operations, overlap certain operations, or some combination thereof. It should be understood that unless disclosed otherwise, any process illustrated in any flow diagram herein or otherwise illustrated or described herein may be performed by a machine, mechanism, and/or computing system 1500 discussed herein, and may be performed automatically (e.g., in response to one or more triggers/conditions described herein), autonomously, semi-autonomously (e.g., based on received instructions), or a combination thereof. Furthermore, any action described herein as occurring in response to one or more particular triggers/conditions should be understood to optionally occur automatically response to the one or more particular triggers/conditions.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method of generating and processing simulated patient information, the method comprising:
    receiving feature parameters and one or more possible outcomes, wherein the feature parameters and the one or more possible outcomes both correspond to features, wherein each feature parameter of the feature parameters identifies a distribution of possible values for one feature of the features, wherein the features include one or more patient characteristics, wherein the one or more possible outcomes include one or more possible diagnoses corresponding to the features;
    generating, based on the feature parameters and the one or more possible outcomes, a simulated patient population dataset that includes a plurality of simulated patient datasets, wherein each simulated patient dataset of the plurality of simulated patient datasets represents one simulated patient and includes feature values randomly selected according to the distribution of possible values that respectively correspond to each feature;
    generating at least one machine learning model by training the at least one machine learning model using training data, wherein the training data includes at least the simulated patient population dataset, wherein the at least one machine learning model includes one or more decision trees having nodes, wherein a first subset of the nodes corresponds to specific features of the features, wherein a second subset of the nodes corresponds to at least one specific outcome of the one or more possible outcomes, wherein at least a first node of the nodes corresponds to a symptom, wherein at least a second node of the nodes corresponds to a diagnosis, wherein a query dataset identifies query feature values for the features associated with a query patient, wherein the at least one machine learning model is configured to generate one or more respective outcome probabilities of each of one or more predicted outcomes in response to input of the query dataset into the at least one machine learning model, wherein the one or more predicted outcomes includes at least a subset of the one or more possible outcomes, wherein the one or more respective outcome probabilities include a first outcome probability determined using the at least one machine learning model based on the query dataset and a second outcome probability determined using the at least one machine learning model based on the query dataset;
    identifying a difference between the first outcome probability and the second outcome probability;
    determining that the difference is below a threshold; and
    adding an additional feature value to the query dataset based on the difference being below a threshold.

2. The method of claim 1, wherein the features include one or more possible symptoms, wherein the feature values associated with a simulated patient dataset identify whether the one or more possible symptoms are present in the simulated patient dataset, and wherein the symptom is one of the one or more possible symptoms.

3. The method of claim 1, wherein the one or more predicted outcomes include a predicted diagnosis, and wherein the one or more respective outcome probabilities include a corresponding diagnosis probability for the predicted diagnosis.

4. The method of claim 1, wherein the at least one machine learning model identifies at least one of a recommendation for a test of a query patient for gathering an additional feature value for the query dataset that helps to differentiate between two of the one or more respective outcome probabilities or a recommendation to add one or more additional feature values to the query dataset.

5. The method of claim 1, further comprising:
    receiving the query dataset;
    generating the one or more predicted outcomes and the one or more respective outcome probabilities using the at least one machine learning model based on the query feature values of the query dataset; and
    providing the one or more predicted outcomes and the one or more respective outcome probabilities to a query device.

6. The method of claim 5, further comprising:
    receiving feedback from the query device in response to providing the one or more predicted outcomes and the one or more respective outcome probabilities to the query device, wherein the feedback disputes accuracy of at least one of the one or more predicted outcomes or at least one of the one or more respective outcome probabilities; and
    updating the at least one machine learning model based on the feedback.

7. The method of claim 1, wherein the one or more decision trees relate the feature parameters to the one or more predicted outcomes and the one or more respective outcome probabilities.

8. The method of claim 1, wherein the one or more possible outcomes include at least a first outcome and a second outcome, wherein the one or more decision trees include at least a first decision tree and a second decision tree, wherein the first decision tree identifies a first set of one or more decisions that the at least one machine learning model uses to determine whether to include the first outcome within the one or more predicted outcomes and whether to include a first outcome probability associated with the first outcome in the one or more respective outcome probabilities, wherein the second decision tree identifies a second set of one or more decisions that the at least one machine learning model uses to determine whether to include the second outcome within the one or more predicted outcomes and whether to include a second outcome probability associated with the second outcome in the one or more respective outcome probabilities.

9. The method of claim 1, further comprising:
    receiving a second set of feature parameters and a second set of possible outcomes, wherein the second set of feature parameters and the second set of possible outcomes both correspond to a second set of features, wherein each feature parameter of the second set of feature parameters identifies a corresponding distribution of possible values for one feature of the second set of features;
    generating, based on the second set of feature parameters and the second set of possible outcomes, a second simulated patient population dataset that includes a second plurality of simulated patient datasets, wherein each simulated patient dataset of the second plurality of simulated patient datasets includes a second set of feature values randomly selected according to the corresponding distribution identified in each feature parameter of the second set of feature parameters; and
    generating a second machine learning model by training the second machine learning model using a second set of training data, wherein the second set of training data includes the second simulated patient population dataset, wherein the second machine learning model and the at least one machine learning model are configured to generate the one or more respective outcome probabilities of each of the one or more predicted outcomes.

10. The method of claim 1, wherein the at least one machine learning model includes a first machine learning model and a second machine learning model, wherein the first outcome probability is determined using the first machine learning model based on the query dataset, and wherein the second outcome probability is determined using the second machine learning model based on the query dataset, further comprising:
tuning, based on the difference, at least one of the first machine learning model or the second machine learning model.

11. The method of claim 1, wherein the one or more predicted outcomes include a recommended treatment and a recommendation strength corresponding to the recommended treatment.

12. The method of claim 1, wherein receiving the feature parameters and one or more possible outcomes includes parsing at least one information source using a natural language processing (NLP) algorithm to identify the feature parameters and one or more possible outcomes, wherein the at least one information source is associated with an expert who is associated with an expert reputation score, wherein generating the simulated patient population dataset includes generating a simulated patient population reputation score corresponding to the simulated patient population dataset, wherein the simulated patient population reputation score is based on the expert reputation score, wherein the training data includes at least at least one of the expert reputation score or the simulated patient population reputation score.

13. The method of claim 12, further comprising:
updating the at least one machine learning model and at least one of the simulated patient population reputation score or the expert reputation score based on feedback associated with at least one of the one or more respective outcome probabilities or the one or more predicted outcomes.

14. The method of claim 1, further comprising:
tuning the at least one machine learning model based on at least one of the one or more predicted outcomes or feedback associated with the one or more predicted outcomes.

15. The method of claim 1, further comprising:
modifying the simulated patient population dataset to generate a modified simulated patient population dataset;
generating at least one secondary machine learning model based on the modified simulated patient population dataset, wherein the at least one secondary machine learning model is configured to generate a second set of one or more respective outcome probabilities in response to input of the query dataset into the at least one secondary machine learning model; and
tuning the at least one machine learning model based on cross-validation of the at least one machine learning model.

16. The method of claim 1, wherein the at least one machine learning model includes at least one of a neural network, a deep learning algorithm, a random forest, a gradient boosting algorithm, a support vector machine, a k-Nearest Neighbors (kNN) algorithm, or a k-means algorithm.

17. The method of claim 1, further comprising:
ranking the one or more predicted outcomes in order of the one or more respective outcome probabilities.

18. The method of claim 1, further comprising:
determining respective levels of importance of a query feature value of the query feature values to determining the one or more predicted outcomes and the one or more respective outcome probabilities based on an effect of the query feature value on the one or more respective outcome probabilities.

19. The method of claim 1, further comprising:
determining a level of importance of a feature based on a difference that removing the feature from consideration by the at least one machine learning model causes to the one or more respective outcome probabilities.

20. The method of claim 19, further comprising:
requesting an additional feature value associated with the feature based on the level of importance of the feature; and
adding the additional feature value to the query dataset.

21. The method of claim 1, wherein the at least one machine learning model includes a first machine learning model and a second machine learning model, wherein the first machine learning model is used to determine a first outcome probability of at least one first predicted outcome, wherein the second machine learning model is used for prediction of a second outcome probability of at least one second predicted outcome, wherein the one or more predicted outcomes includes the at least one first predicted outcome and the at least one second predicted outcome, and wherein the one or more respective outcome probabilities include the first outcome probability and the second outcome probability.

22. The method of claim 1, further comprising:
identifying a probability of a specific outcome of the one or more possible outcomes, wherein the simulated patient population dataset is generated with a proportion of the plurality of simulated patient datasets having the specific outcome, wherein the proportion is based on the probability.

23. The method of claim 22, wherein the probability is specific to a specified population having a specified characteristic.

24. The method of claim 1, further comprising:
recommending addition of a second additional feature value to the query dataset.

25. The method of claim 1, further comprising:
receiving an input; and
interpreting the input using a natural language processing (NLP) algorithm to receive the feature parameters corresponding to the features, to identify the features, or to identify at least one of the one or more possible outcomes.

26. The method of claim 1, wherein at least one of the one or more predicted outcomes is indicative of a level of healthiness in the query patient, wherein the level of healthiness falls within a range of at least two possible healthiness level values.

27. The method of claim 1, further comprising:
generating a multiple-choice question, wherein generating the multiple-choice question includes:
selecting a specific simulated patient dataset from the simulated patient population dataset,
querying the at least one machine learning model with feature values specific to the specific simulated patient dataset to obtain one or more predicted simulated patient outcomes, and identifying one or more answers to the multiple-choice question based on the obtained one or more predicted simulated patient outcomes.

28. The method of claim 1, wherein the additional feature value is gathered using a test, and wherein the additional feature value shifts at least one of the one or more respective outcome probabilities of the one or more predicted outcomes to increase the difference to exceed the threshold.

29. The method of claim 1, further comprising:
receiving metadata associated with at least one information source, wherein receiving the feature parameters and one or more possible outcomes includes parsing at least one information source using a natural language processing (NLP) algorithm to identify the feature parameters and one or more possible outcome; and
determining a simulated patient population reputation score based on the metadata, wherein the simulated patient population reputation score corresponds to the simulated patient population dataset, and wherein the training data includes the simulated patient population reputation score.

30. The method of claim 29, further comprising:
updating the at least one machine learning model and the simulated patient population reputation score based on feedback associated with at least one of the one or more respective outcome probabilities or the one or more predicted outcomes.

31. The method of claim 1, further comprising:
identifying a test based on the feature parameters, wherein at least a subset of the plurality of simulated patient datasets in the simulated patient population dataset include one or more specific feature values associated with the test.

32. The method of claim 1, wherein receiving the feature parameters and one or more possible outcomes includes parsing at least one information source using a natural language processing (NLP) algorithm to identify the feature parameters and one or more possible outcomes, wherein the NLP algorithm identifies the one or more possible outcomes based on parsing at least one mention of a patient with the one or more possible outcomes in the at least one information source, and wherein the NLP algorithm determines at least one of the feature parameters for at least one of the features based on at least one patient feature value of the patient in the at least one information source.

33. The method of claim 1, further comprising:
receiving additional information, wherein the additional information includes at least one of an additional feature parameter or an additional possible outcome;
enrich the simulated patient population dataset based on the additional information to generate an enriched simulated patient population dataset, wherein enriching the simulated patient population dataset includes at least one of adding at least one additional simulated patient dataset into the simulated patient population dataset, updating the simulated patient population dataset based on the feature parameters, updating the simulated patient population dataset based on the additional possible outcome, or updating the simulated patient population dataset based on an additional feature; and
updating the at least one machine learning model based on the enriched simulated patient population dataset.

34. The method of claim 33, wherein the additional information is associated with an additional feature, and wherein the additional information includes information about a level of importance of the additional feature in predicting at least one of the additional possible outcome or the one or more possible outcomes.

35. The method of claim 1, wherein the at least one machine learning model includes a first machine learning model and a second machine learning model, wherein the first outcome probability is determined using the first machine learning model based on the query dataset, and wherein the second outcome probability is determined using the second machine learning model based on the query dataset.

36. A system that generates and processes simulated patient information, the system comprising:
one or more memory units storing instructions; and
one or more processors executing the instructions, wherein execution of the instructions by the one or more processors cause the one or more processors to:
receive feature parameters and one or more possible outcomes, wherein the feature parameters and the one or more possible outcomes both correspond to features, wherein each feature parameter of the feature parameters identifies a distribution of possible values for one feature of the features, wherein the features include one or more patient characteristics, wherein the one or more possible outcomes include one or more possible diagnoses corresponding to the features;
generate, based on the feature parameters and the one or more possible outcomes, a simulated patient population dataset that includes a plurality of simulated patient datasets, wherein each simulated patient dataset of the plurality of simulated patient datasets represents one simulated patient and includes feature values randomly selected according to the distribution of possible values that respectively correspond to each feature;
generate at least one machine learning model by training the at least one machine learning model using training data, wherein the training data includes at least the simulated patient population dataset, wherein the at least one machine learning model includes one or more decision trees having nodes, wherein a first subset of the nodes corresponds to specific features of the features, wherein a second subset of the nodes corresponds to at least one specific outcome of the one or more possible outcomes, wherein at least a first node of the nodes corresponds to a symptom, wherein at least a second node of the nodes corresponds to a diagnosis, wherein a query dataset identifies query feature values for the features associated with a query patient, wherein the at least one machine learning model is configured to generate one or more respective outcome probabilities of each of one or more predicted outcomes in response to input of the query dataset into the at least one machine learning model, wherein the one or more predicted outcomes includes at least a subset of the one or more possible outcomes, wherein the one or more respective outcome probabilities include a first outcome probability determined using the at least one machine learning model based on the query dataset and a second outcome probability determined using the at least one machine learning model based on the query dataset;
identify a difference between the first outcome probability and the second outcome probability;
determine that the difference is below a threshold; and add an additional feature value to the query dataset based on the difference being below a threshold.

37. The system of claim 36, further comprising a database, wherein the simulated patient population dataset is stored in the database.

38. The system of claim 36, wherein the features include one or more possible symptoms, wherein the feature values associated with a simulated patient dataset identify whether the one or more possible symptoms are present in the simulated patient dataset, and wherein the symptom is one of the one or more possible symptoms.

39. The system of claim 38, wherein the at least one machine learning model includes at least one of a neural network, a deep learning algorithm, a random forest, a gradient boosting algorithm, a support vector machine, a k-Nearest Neighbors (kNN) algorithm, or a k-means algorithm.

40. The system of claim 36, wherein the one or more predicted outcomes include a predicted diagnosis, and wherein the one or more respective outcome probabilities include a corresponding diagnosis probability for the predicted diagnosis.

41. The system of claim 36, wherein execution of the instructions by the one or more processors causes the one or more processors to:
   receive the query dataset;
   generate the one or more predicted outcomes and the one or more respective outcome probabilities using the at least one machine learning model based on the query feature values of the query dataset; and
   provide the one or more predicted outcomes and the one or more respective outcome probabilities to a query device.

42. The system of claim 41, wherein execution of the instructions by the one or more processors causes the one or more processors to:
   receive feedback from the query device in response to providing the one or more predicted outcomes and the one or more respective outcome probabilities to the query device, wherein the feedback disputes accuracy of at least one of the one or more predicted outcomes or at least one of the one or more respective outcome probabilities; and
   tune the at least one machine learning model based on the feedback.

43. The system of claim 36, wherein the one or more decision trees relate the feature parameters to the one or more predicted outcomes.

44. The system of claim 36, wherein execution of the instructions by the one or more processors causes the one or more processors to:
   generate a second machine learning model by training the second machine learning model using a second set of training data, wherein the second set of training data includes a second patient population dataset distinct from the simulated patient population dataset, wherein the second machine learning model and the at least one machine learning model are configured to generate the one or more respective outcome probabilities of each of the one or more predicted outcomes.

45. The system of claim 36, wherein the at least one machine learning model uses a random forest algorithm.

46. A non-transitory computer readable storage medium having embodied thereon a program, wherein the program is executable by a processor to perform a method of generating and processing simulated patient information, the method comprising:
   receiving feature parameters and one or more possible outcomes, wherein the feature parameters and the one or more possible outcomes both correspond to features, wherein each feature parameter of the feature parameters identifies a distribution of possible values for one feature of the features, wherein the features include one or more patient characteristics, wherein the one or more possible outcomes include one or more possible diagnoses corresponding to the features;
   generating, based on the feature parameters and the one or more possible outcomes, a simulated patient population dataset that includes a plurality of simulated patient datasets, wherein each simulated patient dataset of the plurality of simulated patient datasets represents one simulated patient and includes feature values randomly selected according to the distribution of possible values that respectively correspond to each feature;
   generating at least one machine learning model by training the at least one machine learning model using training data, wherein the training data includes at least the simulated patient population dataset, wherein the at least one machine learning model includes one or more decision trees having nodes corresponding to different respective probabilities, wherein a first subset of the nodes corresponds to specific features of the features, wherein a second subset of the nodes corresponds to at least one specific outcome of the one or more possible outcomes, wherein at least a first node of the nodes corresponds to a symptom, wherein at least a second node of the nodes corresponds to a diagnosis, wherein a query dataset identifies query feature values for the features associated with a query patient, wherein the at least one machine learning model is configured to generate one or more respective outcome probabilities of each of one or more predicted outcomes in response to input of the query dataset into the at least one machine learning model, wherein the one or more predicted outcomes includes at least a subset of the one or more possible outcomes, wherein the one or more respective outcome probabilities include a first outcome probability determined using the at least one machine learning model based on the query dataset and a second outcome probability determined using the at least one machine learning model based on the query dataset;
   identifying a difference between the first outcome probability and the second outcome probability;
   determining that the difference is below a threshold; and
   adding an additional feature value to the query dataset based on the difference being below a threshold.

47. A method of generating and processing simulated patient information, the method comprising:
   receiving feature parameters and one or more possible outcomes, wherein the feature parameters and the one or more possible outcomes both correspond to features, wherein each feature parameter of the feature parameters identifies a distribution of possible values for one feature of the features, wherein the features include one or more patient characteristics, wherein the one or more possible outcomes include one or more possible diagnoses corresponding to the features;
   generating, based on the feature parameters and the one or more possible outcomes, a simulated patient population dataset that includes a plurality of simulated patient datasets, wherein each simulated patient dataset of the plurality of simulated patient datasets represents one simulated patient and includes feature values randomly selected according to the distribution of possible values that respectively correspond to each feature;

generating at least one machine learning model by training the at least one machine learning model using training data, wherein the training data includes at least the simulated patient population dataset, wherein the at least one machine learning model includes one or more decision trees having nodes, wherein a first subset of the nodes corresponds to specific features of the features, wherein a second subset of the nodes corresponds to at least one specific outcome of the one or more possible outcomes, wherein at least a first node of the nodes corresponds to a symptom, wherein at least a second node of the nodes corresponds to a diagnosis, wherein a query dataset identifies query feature values for the features associated with a query patient, wherein the at least one machine learning model is configured to generate one or more respective outcome probabilities of each of one or more predicted outcomes in response to input of the query dataset into the at least one machine learning model, wherein the one or more predicted outcomes includes at least a subset of the one or more possible outcomes; and generating a multiple-choice question, wherein generating the multiple-choice question includes:
selecting a specific simulated patient dataset from the simulated patient population dataset;
querying the at least one machine learning model with feature values specific to the specific simulated patient dataset to obtain one or more predicted simulated patient outcomes; and
identifying one or more answers to the multiple-choice question based on the obtained one or more predicted simulated patient outcomes.

48. The method of claim 47, wherein the features include one or more possible symptoms, wherein the feature values associated with a simulated patient dataset identify whether the one or more possible symptoms are present in the simulated patient dataset, and wherein the symptom is one of the one or more possible symptoms.

49. The method of claim 47, wherein the one or more predicted outcomes include a predicted diagnosis, and wherein the one or more respective outcome probabilities include a corresponding diagnosis probability for the predicted diagnosis.

50. The method of claim 47, wherein the at least one machine learning model identifies at least one of a recommendation for a test of a query patient for gathering an additional feature value for the query dataset that helps to differentiate between two of the one or more respective outcome probabilities or a recommendation to add one or more additional feature values to the query dataset.

51. The method of claim 47, further comprising:
receiving the query dataset;
generating the one or more predicted outcomes and the one or more respective outcome probabilities using the at least one machine learning model based on the query feature values of the query dataset; and
providing the one or more predicted outcomes and the one or more respective outcome probabilities to a query device.

52. The method of claim 51, further comprising:
receiving feedback from the query device in response to providing the one or more predicted outcomes and the one or more respective outcome probabilities to the query device, wherein the feedback disputes accuracy of at least one of the one or more predicted outcomes or at least one of the one or more respective outcome probabilities; and
updating the at least one machine learning model based on the feedback.

53. The method of claim 47, wherein the one or more decision trees relate the feature parameters to the one or more predicted outcomes and the one or more respective outcome probabilities.

54. The method of claim 47, wherein the one or more possible outcomes include at least a first outcome and a second outcome, wherein the one or more decision trees include at least a first decision tree and a second decision tree, wherein the first decision tree identifies a first set of one or more decisions that the at least one machine learning model uses to determine whether to include the first outcome within the one or more predicted outcomes and whether to include a first outcome probability associated with the first outcome in the one or more respective outcome probabilities, wherein the second decision tree identifies a second set of one or more decisions that the at least one machine learning model uses to determine whether to include the second outcome within the one or more predicted outcomes and whether to include a second outcome probability associated with the second outcome in the one or more respective outcome probabilities.

55. The method of claim 47, further comprising:
receiving a second set of feature parameters and a second set of possible outcomes, wherein the second set of feature parameters and the second set of possible outcomes both correspond to a second set of features, wherein each feature parameter of the second set of feature parameters identifies a corresponding distribution of possible values for one feature of the second set of features;
generating, based on the second set of feature parameters and the second set of possible outcomes, a second simulated patient population dataset that includes a second plurality of simulated patient datasets, wherein each simulated patient dataset of the second plurality of simulated patient datasets includes a second set of feature values randomly selected according to the corresponding distribution identified in each feature parameter of the second set of feature parameters; and
generating a second machine learning model by training the second machine learning model using a second set of training data, wherein the second set of training data includes the second simulated patient population dataset, wherein the second machine learning model and the at least one machine learning model are configured to generate the one or more respective outcome probabilities of each of the one or more predicted outcomes.

56. The method of claim 47, wherein the at least one machine learning model includes a first machine learning model and a second machine learning model, wherein the one or more respective outcome probabilities include a first outcome probability determined using the first machine learning model based on the query dataset and a second outcome probability determined using the second machine learning model based on the query dataset, further comprising:
identifying a difference between the first probability and the second probability; and
tuning, based on the difference, at least one of the first machine learning model or the second machine learning model.

57. The method of claim 47, wherein the one or more predicted outcomes include a recommended treatment and a recommendation strength corresponding to the recommended treatment.

58. The method of claim 47, wherein receiving the feature parameters and one or more possible outcomes includes parsing at least one information source using a natural language processing (NLP) algorithm to identify the feature parameters and one or more possible outcomes, wherein the at least one information source is associated with an expert who is associated with an expert reputation score, wherein generating the simulated patient population dataset includes generating a simulated patient population reputation score corresponding to the simulated patient population dataset, wherein the simulated patient population reputation score is based on the expert reputation score, wherein the training data includes at least at least one of the expert reputation score or the simulated patient population reputation score.

59. The method of claim 58, further comprising:
updating the at least one machine learning model and at least one of the simulated patient population reputation score or the expert reputation score based on feedback associated with at least one of the one or more respective outcome probabilities or the one or more predicted outcomes.

60. The method of claim 47, further comprising:
tuning the at least one machine learning model based on at least one of the one or more predicted outcomes or feedback associated with the one or more predicted outcomes.

61. The method of claim 47, further comprising:
modifying the simulated patient population dataset to generate a modified simulated patient population dataset;
generating at least one secondary machine learning model based on the modified simulated patient population dataset, wherein the at least one secondary machine learning model is configured to generate a second set of one or more respective outcome probabilities in response to input of the query dataset into the at least one secondary machine learning model; and
tuning the at least one machine learning model based on cross-validation of the at least one machine learning model.

62. The method of claim 47, wherein the at least one machine learning model includes at least one of a neural network, a deep learning algorithm, a random forest, a gradient boosting algorithm, a support vector machine, a k-Nearest Neighbors (kNN) algorithm, or a k-means algorithm.

63. The method of claim 47, further comprising:
ranking the one or more predicted outcomes in order of the one or more respective outcome probabilities.

64. The method of claim 47, further comprising:
determining respective levels of importance of a query feature value of the query feature values to determining the one or more predicted outcomes and the one or more respective outcome probabilities based on an effect of the query feature value on the one or more respective outcome probabilities.

65. The method of claim 47, further comprising:
determining a level of importance of a feature based on a difference that removing the feature from consideration by the at least one machine learning model causes to the one or more respective outcome probabilities.

66. The method of claim 65, further comprising:
requesting an additional feature value associated with the feature based on the level of importance of the feature; and
adding the additional feature value to the query dataset.

67. The method of claim 47, wherein the at least one machine learning model includes a first machine learning model and a second machine learning model, wherein the first machine learning model is used to determine a first outcome probability of at least one first predicted outcome, wherein the second machine learning model is used for prediction of a second outcome probability of at least one second predicted outcome, wherein the one or more predicted outcomes includes the at least one first predicted outcome and the at least one second predicted outcome, and wherein the one or more respective outcome probabilities include the first outcome probability and the second outcome probability.

68. The method of claim 47, further comprising:
identifying a probability of a specific outcome of the one or more possible outcomes, wherein the simulated patient population dataset is generated with a proportion of the plurality of simulated patient datasets having the specific outcome, wherein the proportion is based on the probability.

69. The method of claim 68, wherein the probability is specific to a specified population having a specified characteristic.

70. The method of claim 47, further comprising:
recommending addition of an additional feature value to the query dataset.

71. The method of claim 47, further comprising:
receiving an input; and
interpreting the input using a natural language processing (NLP) algorithm to receive the feature parameters corresponding to the features, to identify the features, or to identify at least one of the one or more possible outcomes.

72. The method of claim 47, wherein at least one of the one or more predicted outcomes is indicative of a level of healthiness in the query patient, wherein the level of healthiness falls within a range of at least two possible healthiness level values.

73. The method of claim 47, wherein an additional feature value gathered using a test shifts the one or more respective outcome probabilities of the one or more predicted outcomes from a first state to a second state, wherein two of the one or more respective outcome probabilities are within a threshold range of each other in the first state, wherein the two of the one or more respective outcome probabilities are outside of the threshold range of each other in the second state.

74. The method of claim 47, further comprising:
receiving metadata associated with at least one information source, wherein receiving the feature parameters and one or more possible outcomes includes parsing at least one information source using a natural language processing (NLP) algorithm to identify the feature parameters and one or more possible outcomes; and
determining a simulated patient population reputation score based on the metadata, wherein the simulated patient population reputation score corresponds to the simulated patient population dataset, and wherein the training data includes the simulated patient population reputation score.

75. The method of claim 74, further comprising:
updating the at least one machine learning model and the simulated patient population reputation score based on feedback associated with at least one of the one or more respective outcome probabilities or the one or more predicted outcomes.

76. The method of claim 47, further comprising:
identifying a test based on the feature parameters, wherein at least a subset of the plurality of simulated patient datasets in the simulated patient population dataset include one or more specific feature values associated with the test.

77. The method of claim 47, wherein receiving the feature parameters and one or more possible outcomes includes parsing at least one information source using a natural language processing (NLP) algorithm to identify the feature parameters and one or more possible outcomes, wherein the NLP algorithm identifies the one or more possible outcomes based on parsing at least one mention of a patient with the one or more possible outcomes in the at least one information source, and wherein the NLP algorithm determines at least one of the feature parameters for at least one of the features based on at least one patient feature value of the patient in the at least one information source.

78. The method of claim 47, further comprising:
receiving additional information, wherein the additional information includes at least one of an additional feature parameter or an additional possible outcome;
enrich the simulated patient population dataset based on the additional information to generate an enriched simulated patient population dataset, wherein enriching the simulated patient population dataset includes at least one of adding at least one additional simulated patient dataset into the simulated patient population dataset, updating the simulated patient population dataset based on the feature parameters, updating the simulated patient population dataset based on the additional possible outcome, or updating the simulated patient population dataset based on an additional feature; and
updating the at least one machine learning model based on the enriched simulated patient population dataset.

79. The method of claim 78, wherein the additional information is associated with an additional feature, and wherein the additional information includes information about a level of importance of the additional feature in predicting at least one of the additional possible outcome or the one or more possible outcomes.

80. The method of claim 47, wherein the at least one machine learning model includes a first machine learning model and a second machine learning model, wherein the one or more respective outcome probabilities include a first outcome probability determined using the first machine learning model based on the query dataset and a second outcome probability determined using the second machine learning model based on the query dataset, further comprising:
identifying a difference between the first outcome probability and the second outcome probability;
determining that the difference is below a threshold; and
adding an additional feature value to the query dataset based on the difference being below the threshold.

* * * * *